United States Patent

Dicesare et al.

Patent Number: 5,904,693
Date of Patent: May 18, 1999

[54] AUTOMATIC LAPAROSCOPIC LIGATION CLIP APPLICATOR

[75] Inventors: Paul C. Dicesare, Norwalk; Jeffrey A. Stein, Milford; William J. Allen, Stratford; Joseph N. Logan, Trumbull; John A. Conners, Fairfield, all of Conn.

[73] Assignee: American Cyanamid Company, Wayne, N.J.

[21] Appl. No.: 08/346,285

[22] Filed: Nov. 23, 1994

Related U.S. Application Data

[63] Continuation-in-part of application No. 08/054,770, Apr. 27, 1993, abandoned.

[51] Int. Cl.$^6$ ............................................... A61B 17/00
[52] U.S. Cl. ........................... 606/143; 606/139; 227/901
[58] Field of Search .................................. 606/139, 142, 606/143; 227/175.1–182.1, 19, 901

[56] References Cited

U.S. PATENT DOCUMENTS

| | | |
|---|---|---|
| 3,882,854 | 5/1975 | Hulka et al. . |
| 4,299,224 | 11/1981 | Noiles ..................................... 606/143 |
| 4,325,377 | 4/1982 | Boebel . |
| 4,425,915 | 1/1984 | Ivanov . |
| 4,448,193 | 5/1984 | Ivanov . |
| 4,509,518 | 4/1985 | McGarry et al. . |
| 4,576,166 | 3/1986 | Montgomery et al. . |
| 4,590,937 | 5/1986 | Daniega . |
| 4,598,711 | 7/1986 | Daniega . |
| 4,624,254 | 11/1986 | McGarry et al. ....................... 606/143 |
| 4,662,373 | 5/1987 | Montgomery et al. . |
| 4,759,364 | 7/1988 | Boebel . |
| 5,047,038 | 9/1991 | Peters et al. ............................. 606/139 |
| 5,084,057 | 1/1992 | Green et al. ............................. 606/142 |
| 5,099,827 | 3/1992 | Melzer et al. . |
| 5,100,420 | 3/1992 | Green et al. ............................. 606/143 |
| 5,116,349 | 5/1992 | Aranyi ..................................... 606/142 |
| 5,129,885 | 7/1992 | Green et al. ............................. 604/164 |
| 5,171,247 | 12/1992 | Hughett et al. ......................... 606/142 |
| 5,171,249 | 12/1992 | Stefanchik et al. ..................... 606/142 |
| 5,282,811 | 2/1994 | Booker et al. .......................... 606/143 |
| 5,289,963 | 3/1994 | McGarry et al. ....................... 606/143 |
| 5,306,283 | 4/1994 | Conners .................................. 606/151 |
| 5,354,304 | 10/1994 | Allen et al. ............................. 606/142 |
| 5,389,102 | 2/1995 | Green et al. ............................. 606/143 |
| 5,395,034 | 3/1995 | Allen et al. ........................... 227/178.1 |
| 5,395,381 | 3/1995 | Green et al. ............................. 606/143 |
| 5,403,327 | 4/1995 | Thornton et al. ....................... 606/143 |
| 5,423,471 | 6/1995 | Mastri et al. ......................... 227/175.1 |
| 5,445,167 | 8/1995 | Yoon et al. .............................. 606/143 |

FOREIGN PATENT DOCUMENTS 0510826  10/1992  European Pat. Off. .

Primary Examiner—Jeffrey A. Schmidt
Attorney, Agent, or Firm—Fitzpatrick, Cella, Harper & Scinto

[57] ABSTRACT

A laparoscopic ligation clip applicator for automatically applying a plurality of ligation clips includes a handle assembly having an actuator, an elongated shaft connected to the handle assembly, and an actuating mechanism disposed within the shaft. The actuating mechanism includes a clamp for engaging a first piece of the ligation clip and a slidable driver for driving a second piece of the ligation clip relative to the first piece. The actuating mechanism also includes a hold for preventing rearward movement of the ligation clips, and an advancer for sequentially feeding the ligation clips. A slidable cam, operably connected to the handle assembly, actuates the clamp, the driver and the advancer.

50 Claims, 12 Drawing Sheets

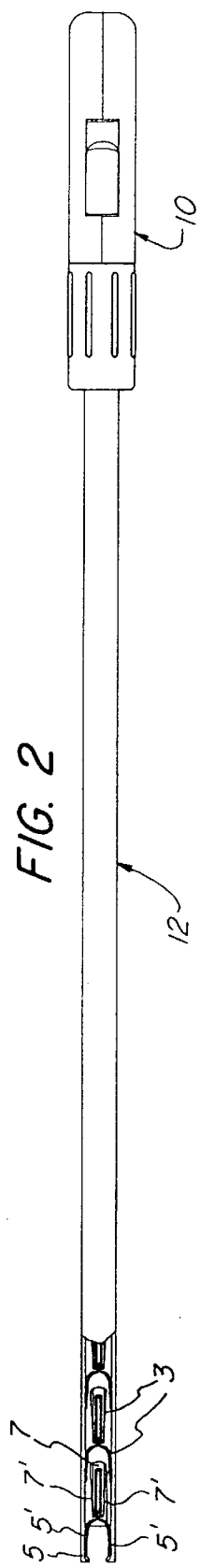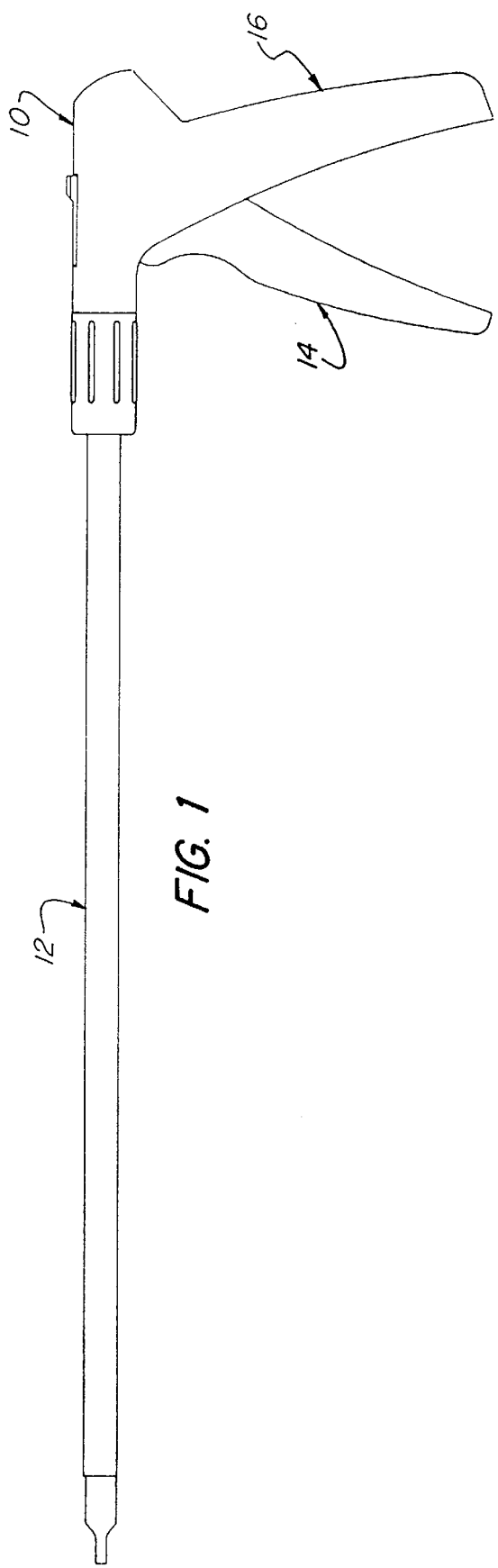

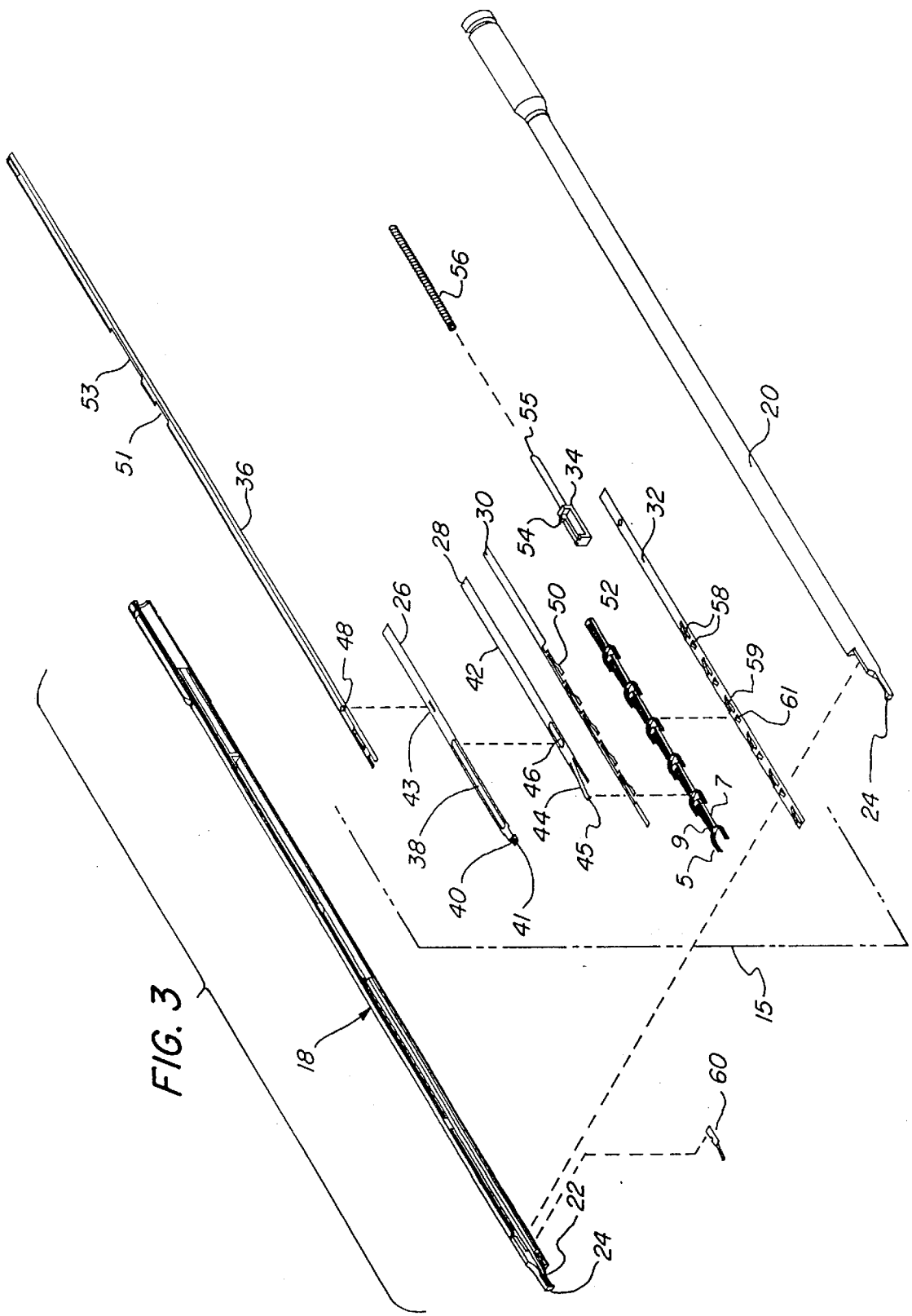

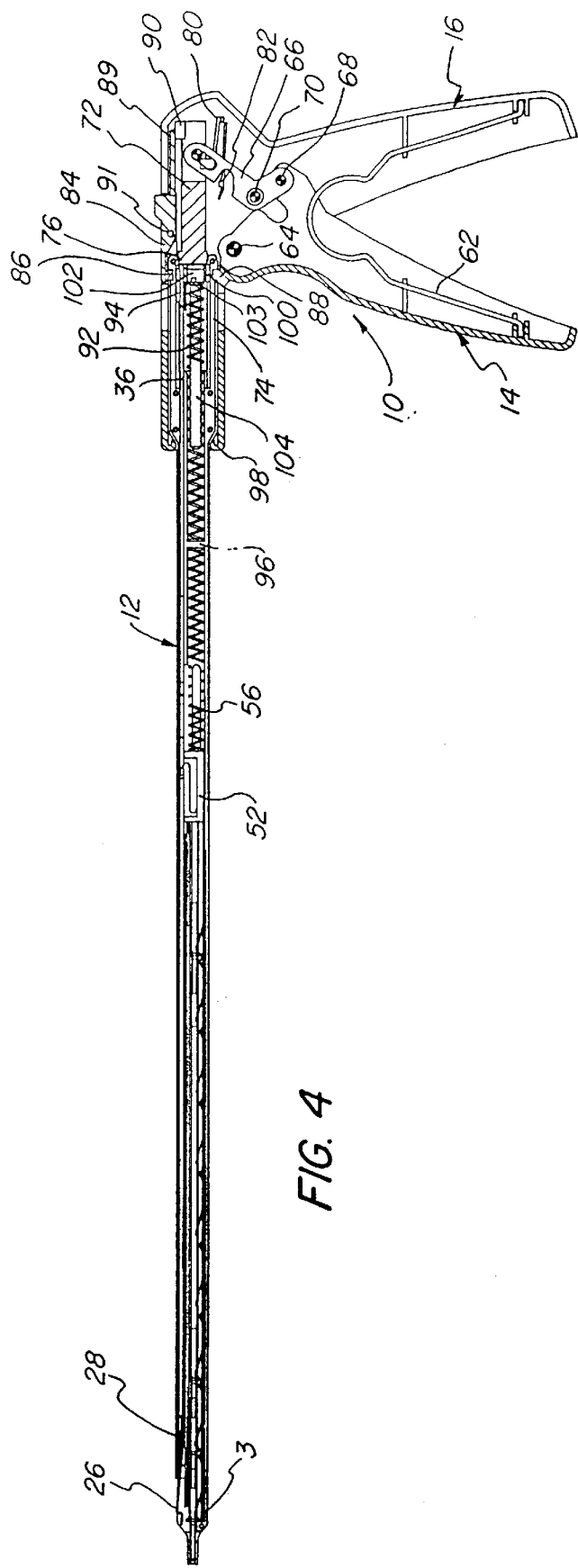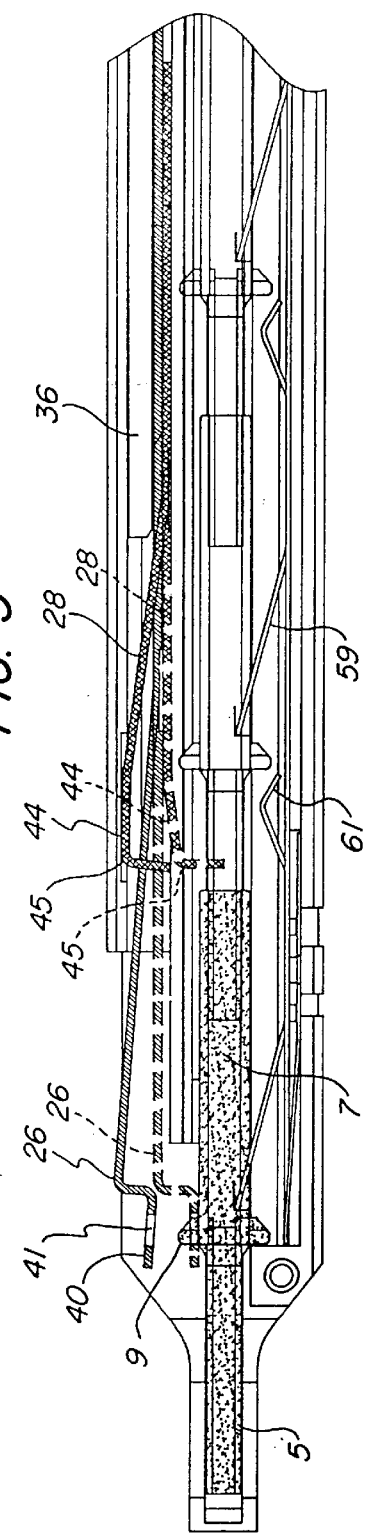

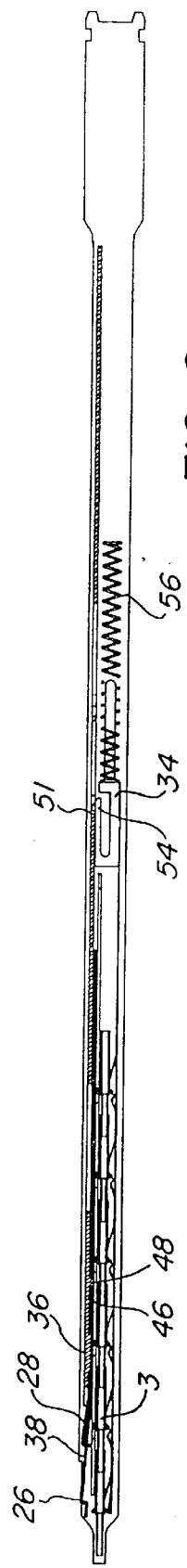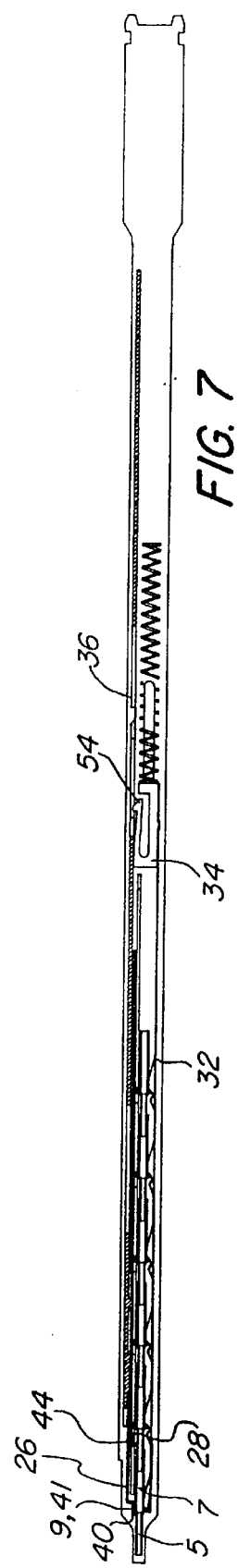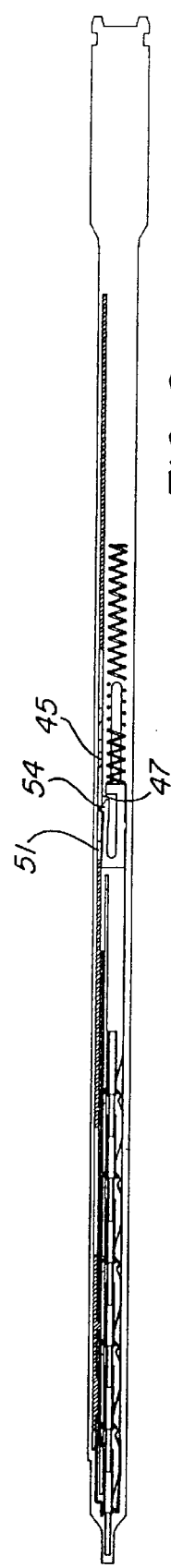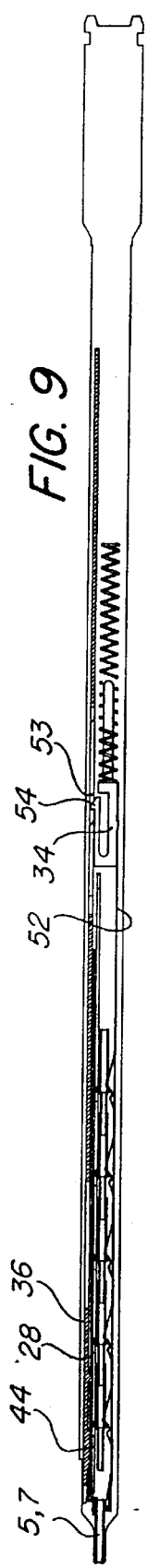

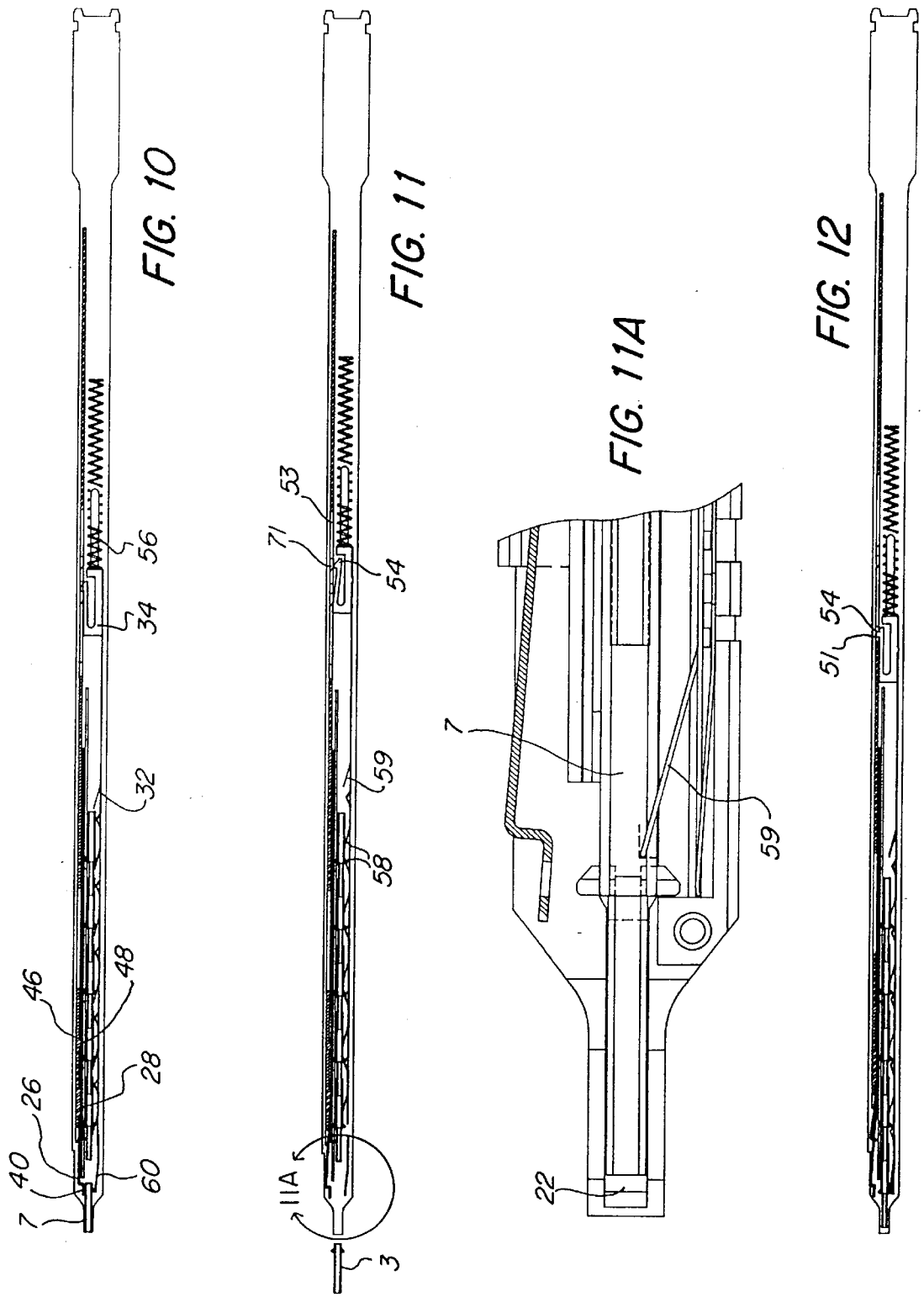

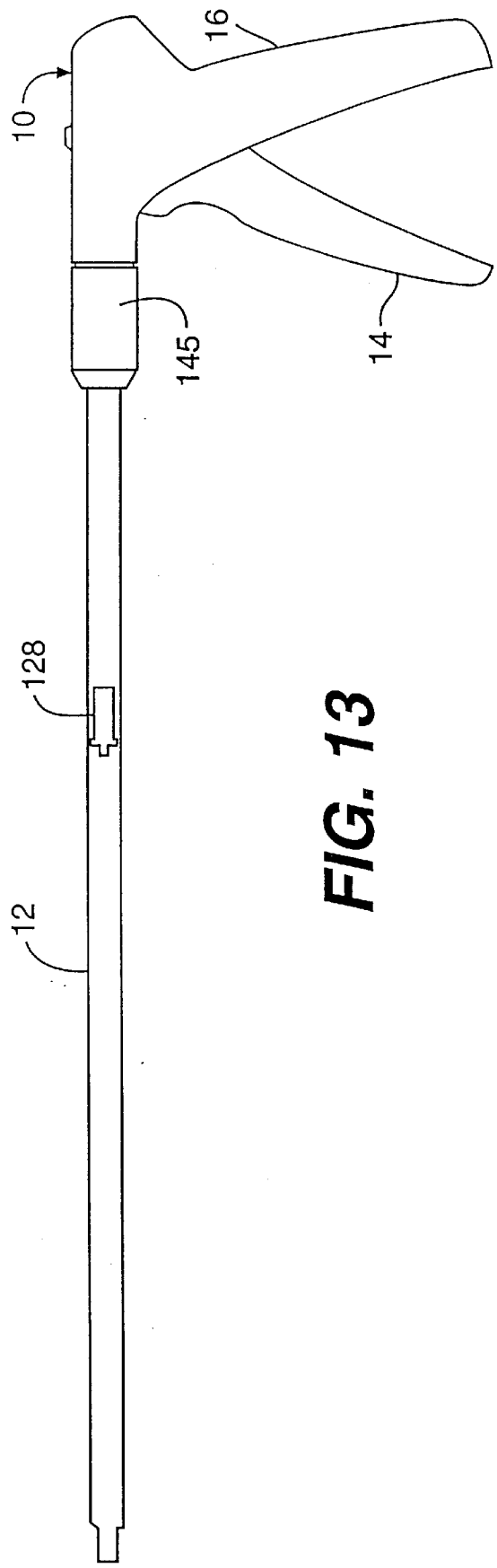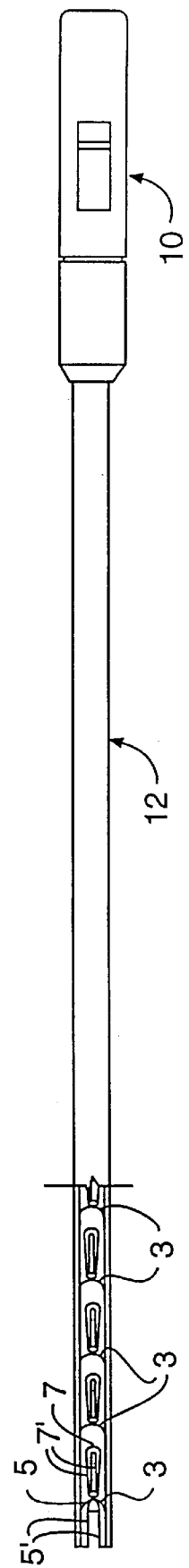
FIG. 13
FIG. 14

AUTOMATIC LAPAROSCOPIC LIGATION CLIP APPLICATOR

CROSS-REFERENCE TO RELATED APPLICATION

This application is a continuation-in-part of U.S. application Ser. No. 08/054,770, filed Apr. 27, 1993, now abandoned.

BACKGROUND OF THE INVENTION

1. Field of the Invention

The present invention relates generally to a medical instrument for use with one or more surgical ligation clips. More particularly, the invention is directed to a laparoscopic ligation clip applicator for assembling and clamping a two-piece ligation clip and for automatically feeding each of a plurality of ligation clips to be sequentially assembled and clamped.

2. Description of the Prior Art

There are many types of known mechanical applicators for automatically feeding and sequentially closing each of a plurality of conventional ligation clips around a vessel (e.g., a vein, an artery, a cystic duct, and the like.) to be occluded. A conventional ligation clip is typically made of metal and is U-shaped with two extending legs that are bent inwardly by, for example, a known fulcrum type applicator having a scissors-like handle with movable jaws. The jaws close together to crimp the clip about the vessel. Such known applicators house a plurality of ligation clips and automatically feed the clips by using, for example, a biasing mechanism, to sequentially position the ligation clips to be crimped between the movable jaws. Other known ligation clip applicators include movably mounted crimping jaws, and feeding mechanisms for conventional ligation clips, that are actuated remotely through various trigger mechanisms. Such designs are shown in U.S. Pat. No. 4,576,166 (Montgomery, et al.), U.S. Pat. No. 4,662,373 (Montgomery, et al.) and U.S. Pat. No. 4,598,711 (Deniega), all assigned to the assignee of the present invention, and in U.S. Pat. No. 5,084,057 (Green, et al.) and U.S. Pat. No. 5,100,420 (Green, et al.), assigned to United States Surgical Corporation.

However, further improvements for applying surgical ligation clips are desirable, and in particular, an automatic ligation clip applicator is needed for use with unique two-piece ligation clips such as are disclosed in U.S. Pat. Nos. 4,590,937 and 5,306,283. Those ligation clips provide many advantages over known metal clips since they provide superior clamping strength and may be made of bioabsorbable non-metallic materials.

SUMMARY OF THE INVENTION

Accordingly, it is a general object of the present invention to provide an improved automatic ligation clip applicator.

It is another object of the present invention to provide an automatic ligation clip applicator for use with two-piece ligation clips, and more particularly, two-piece ligation clips of the type disclosed in U.S. Pat. Nos. 4,590,937 and 5,306,283.

It is still another object of the present invention to provide an automatic ligation clip applicator that can house and automatically feed a plurality of ligation clips in a forward direction.

It is yet another object of the present invention to provide an automatic clip applicator that can apply a ligation clip using minimally invasive surgery.

In accordance with one aspect of the invention, a ligation clip applicator for applying each of a plurality of sequentially fed two-piece ligation clips comprises a handle assembly having an actuator; an elongated shaft having a proximal end connected to the handle assembly, the shaft housing a plurality of two-piece ligation clips, with a distalmost ligation clip in the shaft disposed in a feed position; and actuating means, disposed within the shaft, for assembling and sequentially feeding the ligation clips. The actuating means includes a clamp for engaging a first piece of the ligation clip disposed in the feed position, a slidable driver for driving a second piece of the ligation clip as the first piece is held stationary, and a slidable cam operably engaged with the clamp and the driver and actuable by actuating the actuator, wherein upon actuation of the cam in a cam-forward stroke the clamp engages the first piece of the ligation clip and holds it stationary and the driver drives the second piece in a forward direction to compress the first piece and close the ligation clip.

Preferably, the slidable cam slides forwardly toward a distal end of the shaft in a cam-forward stroke to advance the driver and the clamp. The cam urges the clamp downwardly to grip the first piece of the ligation clip and the cam also advances the driver to drive the second piece of the ligation clip forwardly and compress the first piece, thus closing the ligation clip.

In one embodiment, the ligation clips are aligned axially in a row within the shaft. A desirable means of sequentially feeding the ligation clips includes a stationary holding device provided with retaining springs and serving as a ratchet-type mechanism to prevent movement of the ligation clips in a rearward direction. The ligation clips are advanced forwardly by an advancer connected to a spring-loaded addrive. The addrive is operably connected to the slidable cam and driven in the rearward direction as the cam slides rearwardly in a cam-return stroke.

The cam is operably connected to the actuator of the handle and advanced in the forward direction by actuation of the actuator. The cam is driven rearwardly by a cam spring positioned in the shaft.

Another feature of the first embodiment is the provision of a ratchet mechanism within the handle. This mechanism prevents release of the actuator until a full cam-forward stroke is completed.

The actuating means within the shaft is compact enough to allow the shaft to fit through a cannula positioned in the patient's body. In this way, the applicator can be manipulated by the surgeon-user from outside of the body and minimally, or non-evasive, surgery can be performed.

Another feature of the subject invention is a flexible latch provided in the handle assembly for engaging the separate elongated shaft. As a safety feature, the latch can only be opened when the handle assembly is not being actuated, that is, in an at-rest position. The elongated shaft may also be disposable. In this way, after firing all of the ligation clips the shaft can be released from the handle and discarded, and can be replaced with a new, sterile shaft pre-loaded with an array of ligation clips.

In accordance with yet another aspect of the invention, a ligation clip applicator for applying a two-piece ligation clip comprises a handle assembly having an actuator, and an elongated shaft having a proximal end connected to the handle assembly and housing a plurality of ligation clips, with a distalmost ligation clip in the shaft disposed in a feed position at a distal end of the shaft. Also provided is ligation clip assembling means, disposed within the shaft, for assembling and closing a designated ligation clip disposed in the feed position; ligation clip feeding means, also disposed within the shaft, for advancing the ligation clips in a forward direction within the shaft and positioning a next-to-distalmost ligation clip in the feed position; and a slidable cam operably connected to the handle assembly for movement in a forward direction in a cam-forward stroke and in a rearward direction in a cam-return stroke. During the cam-forward stroke the slidable cam operably engages the ligation clip assembly means to assemble and close the designated ligation clip, and in the cam-return stroke the cam actuates the ligation clip feeding means to advance the ligation clips.

In accordance with still another aspect of the invention, an automatic laparoscopic ligation clip applicator for applying two-piece ligation clips comprises a handle having a squeezable trigger; an elongated shaft assembly having a proximal end connected to the handle and housing a plurality of two-piece ligation clips arranged in an array, with a distal-most ligation clip in the shaft disposed in a feed position; and a clamp disposed in the shaft assembly for engaging a first piece of a designated ligation clip disposed in the feed position and holding it stationary. In addition, a driver is slidably disposed in the shaft assembly for driving a second piece of the designated ligation clip in the forward direction to compress the stationary first piece and close the designated ligation clip. A holding device is disposed in the shaft assembly and has engaging portions for preventing the array of ligation clips from moving in a rearward direction in the shaft. An advancer is slidably disposed in the shaft assembly for engaging the array of ligation clips and advancing them in a forward direction, and a slidable cam is disposed in the shaft assembly and actuated by the handle to slide in a forward direction in a cam-forward stroke and in a rearward direction in a cam-return stroke. The cam is operably connected to the driver and the advancer.

In accordance with another aspect of the invention, a ligation clip applicator for applying each of a plurality of sequentially fed two-piece ligation clips comprises a handle assembly having an actuator, an elongated shaft having a proximal end connected to the handle assembly, with the shaft housing a plurality of two-piece ligation clips and a distal-most ligation clip in the shaft disposed in a feed position, and actuating means, disposed within the shaft, for assembling and sequentially feeding the ligation clips. The actuating means includes a latch for engaging a first piece of the ligation clip disposed in the feed position, a slidable pusher for pushing a second piece of the ligation clip as the first piece is held stationary, and a slidable push rod operably engaged with the pusher and actuable by operating the actuator. Upon actuation of the push rod in a push rod forward stroke, the latch sequentially engages the first piece of the ligation clip and holds it stationary and the pusher pushes the second piece in a forward direction to compress the first piece and close the ligation clip.

Preferably, the slidable push rod slides forwardly toward a distal end of the shaft in a push rod forward stroke to advance the pusher and lower the latch. The sliding push rod urges the latch downwardly to grip the first piece of the ligation clip and the pusher advances to push the second piece of the ligation clip forwardly and compress the first piece, thus closing the ligation clip.

In this embodiment, the ligation clips are also aligned axially in a row within the shaft. A desirable means of sequentially feeding the ligation clips includes a stationary hold provided with retaining springs and serving as a ratchet-type mechanism to prevent rearward movement of the ligation clips, and a stationary brake for limiting excessive forward movement of the ligation clips. The sequential feeding means also includes an advancer for advancing the ligation clips in the forward direction. The advancer is operably connected to the push rod by a sprocket gear and slides in the opposite direction thereto. Thus, as the push rod is sliding forwardly, the sprocket gear rotates in one direction and forces the advancer to slide in the rearward direction. Conversely, when the push rod is retracted in a push rod return stroke, the advancer slides in the forward direction to advance the array of ligation clips.

The push rod is operably connected to the actuator of the handle and advanced in the forward direction by actuation of the actuator. The push rod is driven rearwardly by an actuator spring positioned in the shaft.

The sprocket gear is rotatably mounted within the shaft and operably connected between the push rod and the advancer. The sprocket gear is preferably formed from first and second gears having offset teeth for engaging correspondingly offset notched portions in the advancer and the push rod. The sprocket gear is rotated by the sliding movement of the push rod to actuate the advancer.

Another feature of this embodiment is the provision of a safety mechanism to ensure that once the push rod is actuated in either the return or forward stroke, that stroke is completed before the other stroke can be initiated. This mechanism prevents premature release of the push rod until a full forward stroke that completely closes a distal most ligation clip is finished.

The safety mechanism includes a triangular pawl mounted in the shaft, with one side pressed against a spring pawl and an opposite apex designed to ride against a ridged portion of the push rod. The ridged portion is flanked on either end by slots which receive the apex of the triangular pawl at the end of each push rod stroke.

The actuating means within the shaft is compact enough to allow the shaft to fit through a cannula positioned in the patient's body. In this way, the applicator can be manipulated by the surgeon-user from outside of the body and minimally, or non-evasive, surgery can be performed.

Another feature of the subject invention is a slot in the shaft for receiving the ligation clips one-by-one. The slot allows easy loading of the ligation clips into the shaft.

Another feature of the subject invention is a flexible latch provided in the handle assembly for engaging the separated elongated shaft. As a safety feature, the latch can only be opened when the handle assembly is not being actuated, that is, in an at-rest position.

In accordance with yet another aspect of the invention, a ligation clip applicator for applying a two-piece ligation clip comprises a handle assembly having an actuator, and an elongated shaft having a proximal end connected to the handle assembly and housing a plurality of ligation clips, with a distal-most ligation clip in the shaft disposed in a feed position at a distal end of the shaft. Also provided is ligation clip assembling means, disposed within the shaft, for assembling and closing a designated ligation clip disposed in the feed position, ligation clip feeding means, also disposed within the shaft, for advancing the ligation clips in a forward direction within the shaft and positioning a next-to-distalmost ligation clip in the feed position, and a slidable push rod operably connected to the handle assembly for movement in a forward direction in a push rod forward stroke and in a rearward direction in a push rod return stroke. During the push rod forward stroke the slidable push rod operably engages the ligation clip assembly means to assemble and close the designated ligation clip, and in the push rod return stroke the push rod actuates the ligation clip feeding means in a forward direction to advance the ligation clips.

In accordance with still another aspect of the invention, an automatic laparoscopic ligation clip applicator for applying two-piece ligation clips comprises a handle having a squeezable trigger, an elongated shaft assembly having a proximal end connected to the handle and housing a plurality of two-piece ligation clips arranged in an array, with a distalmost ligation clip in the shaft disposed in a feed position, and a latch disposed in the shaft assembly for engaging a first piece of a designated ligation clip disposed in the feed position and holding it stationary. In addition, a pusher is slidably disposed in the shaft assembly for driving a second piece of the designated ligation clip in the forward direction to compress the stationary first piece and close the designated ligation clip. A hold is disposed in the shaft assembly and has engaging portions for preventing the array of ligation clips from moving in a rearward direction in the shaft. An advancer is slidably disposed in the shaft assembly for engaging the array of ligation clips and advancing them in a forward direction, and a push rod is disposed in the shaft assembly and actuated by the handle to slide in a forward direction in a push rod forward stroke and in a rearward direction in a push rod return stroke. The push rod is attached at one end to the pusher, and a sprocket gear operably connects the push rod to the advancer.

These and other objects, aspects, features and advantages of the present invention will become apparent from the following detailed description of the preferred embodiments taken in conjunction with the accompanying drawings.

BRIEF DESCRIPTION OF THE DRAWINGS

FIG. 1 is a side elevational view of the automatic laparoscopic ligation clip applicator in accordance with a first embodiment of the present invention showing a shaft and a handle assembly;

FIG. 2 is a top plan view of the automatic laparoscopic ligation clip applicator in accordance with the first embodiment, with a distal end thereof shown partly in cross-section to illustrate a partial array of ligation clips;

FIG. 3 is an exploded view of the automatic laparoscopic ligation clip applicator in accordance with the first embodiment showing the components housed within the shaft;

FIG. 4 is a vertical cross-sectional view of the automatic laparoscopic ligation clip applicator in accordance with the first embodiment of the present invention;

FIG. 5 is an enlarged vertical cross-sectional view of the distal end of the shaft of the automatic laparoscopic ligation clip applicator in accordance with the first embodiment;

FIGS. 6 through 12 are vertical cross-sectional views of the shaft of the automatic laparoscopic ligation clip applicator in accordance with the first embodiment of the present invention illustrating its different operating stages, with FIG. 11A being an isolated enlarged view showing a ligation clip positioned in front of a retaining spring of the applicator;

FIG. 13 is a side elevational view of the automatic laparoscopic ligation clip applicator in accordance with a second embodiment of the present invention showing a shaft portion and a handle assembly;

FIG. 14 is a top plan view of the automatic laparoscopic ligation clip applicator in accordance with the second embodiment, with a distal end thereof shown partly in cross-section to illustrate a partial array of ligation clips;

DESCRIPTION OF THE PREFERRED EMBODIMENTS

Figure 15:
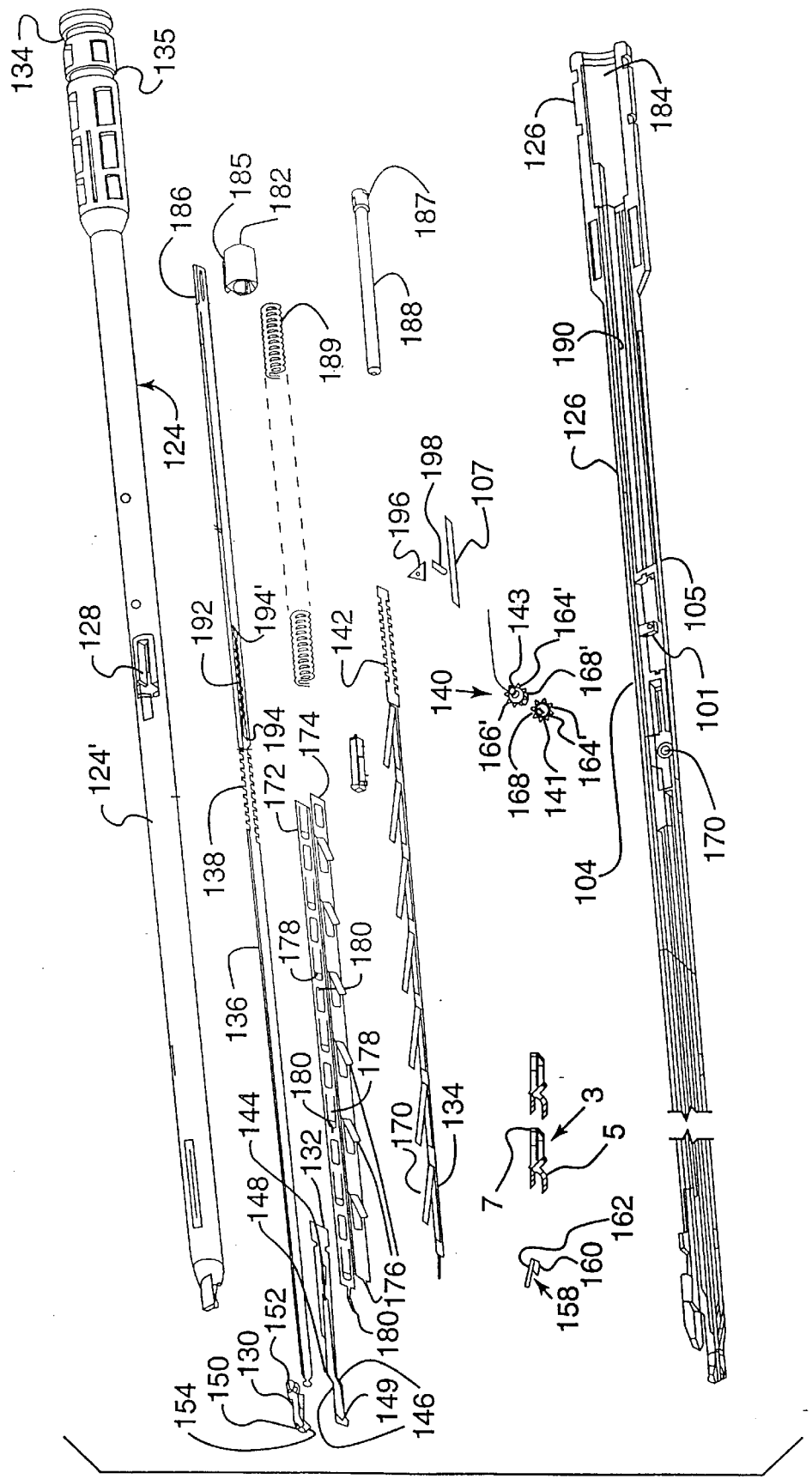
FIG. 15 is an exploded perspective view of the components to be housed in the shaft portion of the automatic laparoscopic ligation clip applicator in accordance with the second embodiment.

For ease of reference, as used herein the term "distal" will refer to that part of the applicator which is farthest from the surgeon-user, and the term "proximal" refers to that part of the applicator which is closest to the surgeon-user.

The automatic laparoscopic ligation clip applicator of the first embodiment of the present invention is shown generally in FIGS. 1 and 2 to comprise a handle assembly 10 and an elongated cylindrical shaft 12 attached to the handle assembly at its proximal end. The handle assembly 10 includes a squeezable trigger 14 and a grip 16. The elongated shaft is preferably of a diameter that allows it to be used in minimally invasive surgery techniques. For example, the shaft may have a diameter of 8 mm so it can fit through a 10 mm cannula communicating from the exterior to the interior of the patient's body.

One of the desirable features of the subject invention is the provision of the shaft 12 and the handle assembly 10 as two separate elements removably connectable together. In this way, a disposable shaft can be used with a reusable handle assembly. The disposable shaft can be easily connected to the handle assembly at any rotational orientation in a manner described below. The disposable shaft is preferably designed for single use/single patient operation and can be discarded after each surgical procedure and replaced with a clean, sterile shaft that is then loaded with a plurality of ligation clips as will also be described below.

A plurality of ligation clips are housed in the shaft as shown in FIG. 2. As noted above, the ligation clip applicator of the present invention is specifically designed to apply two-piece ligation clips of the type described in U.S. Pat. Nos. 4,590,937 and 5,306,283, both of which are incorporated herein by reference. The two-piece ligation clip 3 can be seen in FIGS. 2 and 3 to include a Y-shaped clamp 5 and a U-shaped clip body 7. As explained in detail in U.S. Pat. No. 5,306,283, the ligation clip is closed by drawing the clamp 5 relative to the clip body 7 so that legs 7' of the clip body urge arms 5' of the clamp together to compress and occlude a vessel captured between the arms 5'.

As shown in FIG. 2, the ligation clips are disposed end-to-end in an array within the shaft, with the distalmost ligation clip at the tip of the shaft being in a feed position. Generally speaking, the ligation clip applicator is manipulated to position a designated ligation clip in the feed or application position about a vessel to be occluded, and the handle assembly is actuated to close the designated ligation clip around the vessel. In one complete stroke accomplished by squeezing and releasing the trigger 14, the designated ligation clip at the feed position is closed, ejected from the shaft and the remaining ligation clips are advanced in a forward direction, that is toward the distal tip of the shaft, to sequentially position the next-to-distal-most ligation clip in the feed position.

Generally speaking, the ligation clip applicator is manipulated to position a designated ligation clip in the feed or application position about a vessel to be occluded, and the handle assembly is actuated to close the designated ligation clip around the vessel. In one complete stroke accomplished by squeezing and releasing the trigger, the designated ligation clip at the feed position is closed, ejected from the shaft and the remaining ligation clips are advanced in a forward direction, that is, toward the distal tip of the shaft, to sequentially position the next-to-distal-most ligation clip in the feed position.

The components for actuating the ligation clips, known collectively as the actuating mechanism 15, are shown in FIG. 3. The components are disposed within the shaft 12, which is comprised of two halves, 18 and 20. The two halves of the shaft are keyed to each other and held together by, for example, a shrink tube cover.

Each half of the shaft is provided with axially extending raceways for allowing sliding movement of several of the components within the shaft. More particularly, at the distal end of each half 18 and 20 is a raceway 22 for capturing the ligation clips. The raceway terminates at a chamfered end 24 at the distal tip of the shaft.

The actuating mechanism 15 is comprised of a clamp 26 and driver 28 which work together to assemble and close the designated ligation clip at the feed position, and a holding device 30 and an advancer 32 which work together to sequentially feed the ligation clips in the forward direction. An addrive 34 is connected to the proximal end of the advancer 32. The actuating mechanism further includes a cam 36 for slidably actuating the driver 28 and the advancer 32, through the addrive 34, within the shaft as will be discussed in detail below.

The clamp 26 and the driver 28, which together comprise ligation clip assembly means, work together to assemble and close the ligation clip in the following manner. The clamp 26 is preferably made of a sturdy yet flexible material, such a thin metal, and is shaped to have an elongated slot 38 and a stepped nose portion 40 with an engaging hole 41 for engaging a top post 9 of the Y-shaped clamp 5. A smaller slot 43 in the clamp is used to properly align the clamp within the shaft 12. The driver 28 is also preferably made of a thin, flexible material and comprises a body having a wide portion 42 comparable in width to the clamp 26, and a narrower abutting portion 44 at its distal end with a downturned nose 45 for abutting the clip body 7 and driving it forward. The wide portion includes a slot 46, shorter in length than the extended slot 38 in the clamp, for receiving a pin 48 on the underside of the cam 36.

The clamp 26 is sandwiched between the cam 36 and the driver 28, with the pin 48 extending through the elongated slot 38 in the clamp and slot 46 in the driver. As shown, for example, in FIG. 6, the pin 48 has a width narrower than the length of the slot 46 in the driver and thus a lost motion connection is achieved between the cam 36 and the driver. As the cam 36 slides back and forth within the shaft, the pin 48 engages distal and proximal extremes of the slot 46 in the driver and thus slides the driver in the forward or rearward direction. However, the clamp 26 remains stationary within the shaft, as the extended slot 38 is greater in length than the range of sliding motion of the pin 48.

As best seen in FIG. 5, the distal ends of the clamp 26 and the driver 28, designated by solid lead lines, are bent or inclined upwardly to lie in their unbiased position horizontally above the array of ligation clips. As will be discussed in more detail below, the cam 36 slides forwardly to urge the clamp 26 downwardly and the driver 28 downwardly to assemble and close the designated ligation clip in the feed position.

Returning to FIG. 3, the holding device 30 and advancer 32, which together with the addrive 34 comprise ligation clip feeding means, work together to sequentially advance the array of ligation clips in the forward direction. Both the holding device and the advancer can be made of a thin flexible metal. The holding device 30, which is positioned between the driver 28 and the array of ligation clips, acts like a ratchet mechanism to prevent rearward movement of the ligation clips. This is accomplished by providing a plurality of flexible, downwardly bent leaf springs 50 each secured at its proximal end to the main body of the holding device 30. Each leaf spring is positioned to engage one Y-shaped clamp 5, comprising each ligation clip, from behind and prevents its movement in the rearward direction. When the ligation clips are advanced in the forward direction, the leaf springs are flexed upwardly and do not inhibit such movement. As seen in FIG. 3, the leaf springs 50 are offset from the axial center of the holding device 30 so as not to interfere with the sliding movement of the cam 36 and the driver 28.

The advancer 32 is provided to advance the array of ligation clips by sliding back and forth through its connection to the addrive 34. The addrive includes an addrive head 52 having a latch 54 that operably engages within one of two addrive cut-outs, or slots, 51 and 53 in the cam. The addrive also includes a shaft 55, extending from the addrive head, and a compression spring 56 disposed around the shaft. A plurality of leaf springs 58 are preferably punched out of the thin metal advancer 32. The longer leg 59 of each leaf spring is connected to the advancer at its proximal end and engages one of the ligation clips when the advancer moves forward. The shorter leg 61 of each leaf spring acts as a brake to limit the forward movement of the ligation clips.

To advance the array of ligation clips, the advancer 32 is slid in the rearward direction toward the handle assembly, where the leaf springs 58 are urged downwardly as they slide under the ligation clips. As the advancer is then advanced in the forward direction, the longer leg 59 of each leaf spring engages a lower side of one of the clip bodies 7 and drives the ligation clips forwardly. The forward movement of the advancer moves the ligation clips sequentially forward so the next-to-distal-most ligation clip advances into the feeding position.

FIG. 3 also shows a kick spring 60 that is positioned at the distal end of the shaft below the designated ligation clip at the feed position. The purpose of the kick spring is to eject the assembled ligation clip from the shaft in a manner described in more detail below.

FIG. 4 is a vertical cross-sectional view of the applicator and shows additional details of the handle assembly 10. The trigger 14 is biased to an opened position by a trigger spring 62 and pivots about a pivot point 64. A link 66 is connected to the trigger at pivot point 68 and pivots about pivot point 70 to axially slide an H-drive 72 within a hollow shaft collar 74 of the shaft 12. The H-drive is provided with an abutment end 76 for abutting the proximal end of the cam 36 and an axially slidable spring block 100.

The spring block receives a key head 102 of elongated key 104. The key head includes a tab 103 that slides axially and then laterally in an unshown slot in the interior of the spring block to engage therewith. The key 104 extends axially through a cam spring 92, which rests between stationary wall 96 and the key head 102. A ratchet-type mechanism comprises a latch 80 that moves with the H-drive and a notched grate 82 secured in the handle assembly 10. The notched grate is sloped forwardly and upwardly to bias the latch as it moves with the H-drive in the forward direction. As the trigger 14 is squeezed, the latch 80 rides over the sloped notched grate 82. One or more notches in the grate prevent the biased latch from moving rearwardly, and thus the trigger from being released, until the trigger is fully squeezed. When the trigger is fully squeezed, the latch moves out past the distal tip of the notched grate and is biased to its normal position below the distal tip. As the trigger is released, the latch rides below the notched grate and back to its starting position.

As discussed above, the elongated shaft 12 and the handle assembly are preferably separate elements that can easily be connected together. In this embodiment, a one-piece engagement latch 84 in the handle assembly 10 secures and locks the shaft 12 to the handle assembly. The distal end of the engagement latch is formed with a tooth 86 for engaging an annular groove 88 on the hollow shaft collar 74. At the proximal end of the engagement latch a flexible member 89 engages a block 90 on the proximal end of the H-drive 72. As will be appreciated from the figure, a small space exists between the engagement latch 84 and the H-drive 72. This space allows the flexible member 89 to be depressed so as to pivot the engagement latch 84 about its pivot point 91 and raise the tooth 86 out of engagement with the annular groove 88. As a safety feature, when the H-drive slides in the forward direction, the block 90 moves toward the center of the engagement latch, thus preventing the flexible member from being depressed and locking the shaft to the handle assembly when the trigger is being squeezed. By providing an annular groove 88 on the hollow shaft collar 74 and an abutment end 76 on the H-drive 72, the shaft can be inserted into the handle assembly at any rotational orientation and will still be engaged and actuated by the handle assembly. Cylindrical grip 98 surrounding the collar 74 also allows the shaft to be rotated after engagement to the handle assembly.

FIG. 4 also illustrates the manner in which the cam 36 is actuated. In a cam-forward stroke initiated by squeezing the trigger 14, the H-drive 72 is forced forwardly to abut and slide the cam in the forward direction toward the distal end of the shaft 12. The H-drive abuts the proximal end of the cam, but it is not secured thereto. The spring block 100 is secured to cam 36 by the protrusion of rib 94 through an unshown slot in the cam. As the H-drive 72 is driven in the forward direction by squeezing the trigger, the cam and spring block slide forwardly in the distal direction. This forward motion causes the cam spring 92 to compress and become charged. When the trigger is fully squeezed, the latch 80 comes out of engagement with the notched grate 82, allowing the trigger to be released.

The trigger is released in a cam-return stroke to retract the H-drive back to its rest position. Since the biasing force of the H-drive against the spring block is no longer in effect, the cam spring 92 discharges and pushes the cam 36 in the rearward direction toward the handle assembly.

FIGS. 6 through 12 illustrate the operational steps of the actuating mechanism 15 as the cam is actuated through one complete cam-forward stroke and cam-return stroke. Beginning with FIG. 6, the actuating mechanism of the ligation clip applicator is shown in the rest position, with the cam 36 fully retracted within the shaft and the addrive spring 56 unbiased. Thus, the distal ends of the clamp 26 and driver 28 are bent slightly upwardly in their relaxed positions to rest above a horizontal plane defined by the array of axially-aligned ligation clips 3. The pin 48 on the underside of the cam 36 extends through both the elongated slot 38 in the clamp and the slot 46 in the driver. The pin is shown in FIG. 6 to rest at a rearward end of the slot 46 in the driver. Also in this position, the latch 54 of the addrive 34 is engaged in the first addrive cut out 51 of the cam.

When the trigger is actuated in the cam-forward stroke, the cam begins to slide forwardly as shown in FIG. 7. With this forward motion, a sloped side of the latch 54 is forced downwardly to disengage the addrive 34 from the cam. Therefore, the cam 36 rides over the addrive 34, and the addrive and the advancer 32 remain stationary as the cam moves in the forward direction. At the distal end of the shaft, the sliding cam downwardly urges the distal ends of both the clamp 26 and the driver 28. The nose portion 40 of the clamp is thus lowered to engage the upper post 9 of the Y-shaped clamp 5 of the designated ligation clip by having that post received in the hole 41. The abutting portion 44 of the driver is likewise lowered to a position immediately behind the clip body 7 of the designated ligation clip. In FIG. 5, the clamp and driver are shown in both their normal raised positions by solid lead lines from numbers 26 and 28, respectively, and in their downwardly urged positions by dashed lead lines from numbers 26 and 28, respectively. As will be appreciated, the driver does not slide forwardly with the initial forward movement of the cam 36, because the pin 48 on the cam must first travel the length of the slot 46 in the driver and reach the distal end of the slot as shown in FIG. 8. As the cam continues to slide forwardly, the driver is forced to slide in the forward direction by the pin 48 and abuts the clip body 7, that is the second piece, and pushes it forwardly as the nose portion 40 of the clamp holds the Y-shaped clamp 5, that is the first portion, of the ligation clip stationary.

FIG. 9 shows the completion of the cam-forward stroke. The cam 36 and the driver 28 are in their forwardmost position, with the abutting portion 44 of the driver forcing the clip body 7 around the Y-shaped clamp 5 to close the designated ligation clip. Also at the completion of the cam-forward stroke, the latch 54 of the addrive head 52 engages the second addrive cut-out 53 in the cam. As best shown in FIGS. 8 and 9, when the addrive latch 54 disengages from the first addrive cut-out 51, it rides in a shallow groove 47 underneath the sliding cam until it reaches an abutting portion 44 on the cam. By providing a shallow groove in the cam, reduced stress is applied to the latch 54 as it is urged downwardly and ridden over by the cam. A slanted surface on the abutting portion 44 forces the latch 54 further downwardly as the cam continues to slide in the forward direction past the stationary addrive head 52. The latch 54 pops up into the second addrive cut-out 53 as the cam reaches the end of the cam-forward stroke and engages the addrive with the cam. This point is reached by fully squeezing the trigger and the cam spring 92, although not seen in FIGS. 6 through 12, is compressed and fully charged.

The beginning of the cam-return stroke is shown in FIG. 10. When the trigger 14 is released as discussed above, the compressed cam spring 92 discharges and drives the cam in the rearward direction. As the cam moves rearwardly, it slides over the distal ends of the clamp 26 and the driver 28, and retracts to a position where the distal ends flex upwardly to their rest or normal positions. Lost motion between the cam and the driver takes place as the pin 48 on the cam travels from the distal end of the slot 46 to the proximal end.

When the distal end of the clamp flexes upwardly, the nose portion 40 disengages from the closed ligation clip, and the kick spring 60 biases the ligation clip upwardly and ejects it from the distal end of the shaft as shown in FIG. 11. As will be appreciated, the upward biasing force applied by stationary kick spring cannot eject the ligation clip in the feed position until the ligation clip is assembled and closed. Before that time the clip body 7 is positioned within the raceway 22 and prevented from moving in the vertical direction. Since the addrive 34 is engaged with the cam, rearward movement of the cam pulls the addrive rearwardly to compress and charge the addrive spring 56. The advancer 32 is also pulled rearwardly by its connection to the addrive. The longer legs 59 of the retaining springs 58 on the advancer are flexed downwardly by sliding contact with the ligation clips and move in series to a position behind one of the ligation clips. As the isolation view of FIG. 11A illustrates, the longer legs then flex upwardly to their normal positions and engage a notch in the clip body 7 of one of the ligation clips.

Toward the end of the cam-return stroke, the addrive latch 54 engages a bumper 71 on the interior of the shaft and disengages from the second addrive slot 53 in the cam. When the addrive becomes disengaged from the slot, the addrive spring 56 discharges to advance the addrive and the advancer in the forward direction. The forward movement of the advancer advances each of the ligation clips, and the next-to-most-distal ligation clip is thus advanced forwardly to the feed position at the distal tip of the shaft thereby to become the next designated clip. The addrive latch 54 re-engages with the first addrive slot 51 in the cam and the cam-return stroke is completed.

The automatic laparoscopic ligation clip applicator in accordance with a second embodiment is shown generally in FIGS. 13 and 14 to comprise, as in the first embodiment, a handle assembly 10 and an elongated cylindrical shaft 12 attached to the handle assembly at its proximal end. Like the first embodiment, the cylindrical shaft in the second embodiment is detachably connected to the handle assembly and houses an array of two-piece ligation clips at its distal end.

Figure 16:
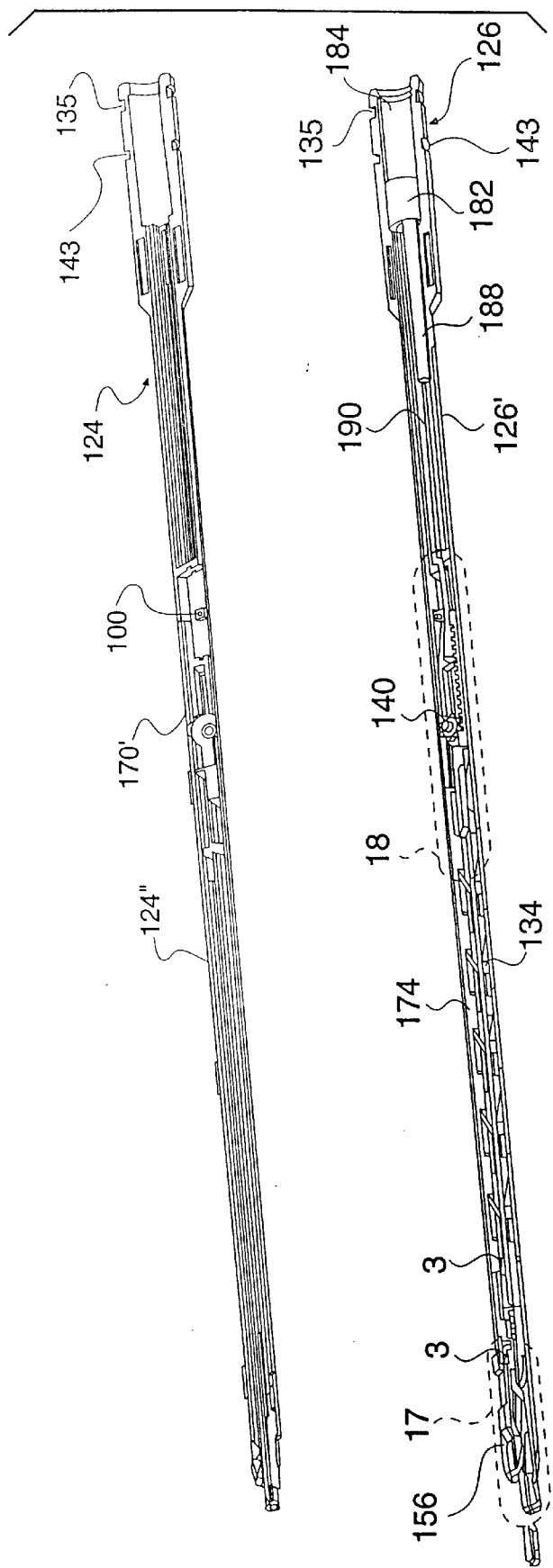
FIG. 16 is an exploded perspective view of the shaft portion of the laparoscopic ligation clip applicator with the components housed in the shaft in accordance with the second embodiment of the present invention.

The components in the second embodiment for actuating the ligation clips, known collectively as the actuating mechanism, are shown in exploded view in FIG. 15 and assembled in the shaft in FIG. 16. These components are house in a left magazine 124 and a right magazine 126 which together form the elongated shaft 12. The shaft itself is preferably made of molded plastic and can be, for example, 16" in length.

FIG. 15 illustrates an outer surface 124' of the left magazine and FIG. 16 illustrates an inner surface 124" of the left magazine 124. The outer surface 124' includes a slot 128 for loading the ligation clips in a manner described in more detail below. The inner surface 124" is provided with axially extending raceways for allowing sliding movement of several of the components and also has contoured surfaces and slots for receiving and securing other components. An inner surface 126' of the right magazine 126 is shown fully loaded with the components in FIG. 16, and an empty inner surface of the right magazine illustrates the various raceways and other contour surfaces for containing the components in FIG. 15. The right and left magazines are keyed to each other and held together by, for example, a shrink tube cover.

The slot 128 in the magazine allows ligation clips to be easily loaded into the shaft. The pre-assembled clips are inserted through the slot 128 in the left magazine 124 when the handle assembly is at rest, i.e., the trigger 14 is not being squeezed. After a first clip is loaded, the applicator is indexed, or fixed, by squeezing and releasing the trigger to advance the first clip in the shaft by one position. Clips are continuously loaded one-by-one into the shaft in the same manner, with the applicator being indexed after each clip is loaded, until the first clip is positioned in the feed position at the distal end of the shaft. In this embodiment, the shaft can hold nine clips. However, because each closed clip is bumped or pushed by the clip immediately behind it to be released from the shaft, only eight clips are used for ligation. The ninth, or last, clip is a dummy clip used only to push the next-to-last clip, i.e., the eighth clip, out of the shaft. The dummy clip has a clip body designed so it cannot be closed, or compressed, when it is advanced to the feed position.

The actuating mechanism includes a pusher 130 and a latch 132 which work together to assemble and close the designated ligation clip at the feed position, and an advancer 134 disposed on an opposite side of, i.e., beneath, the ligation clips for sequentially feeding the ligation clips in the forward direction. The actuating mechanism further includes a push rod 136 that extends substantially the length of the shaft 12 and axially slides therein by actuation of the handle mechanism as discussed below. The push rod includes a double-sided notched position 138 at its central portion for engaging and rotating a sprocket gear 140 as it slides back and forth. The sprocket gear, in turn, engages a double-sided notched portion 142 at the proximal end of the advancer 134 to slide it back and forth.

The pusher 130 and latch 132, which together form ligation clip assembly means, work together to assemble and close the ligation clip in the following manner. The latch 132 is preferably made of a sturdy yet flexible material, such as thin metal, and is formed, such as by stamping, to have an elongated slot 144 defined on either side by rails 146. The rails 146 include a ramp portion 148, and a small notch 149 at the distal end of the slot designed to engage a lug on the clamp 5 of the ligation clip 3 in the feed position. Pusher 130 is keyed to the push rod at its proximal end and slides axially back and forth with the push rod to move relative to the latch 132, which does not slide back and forth in the shaft. The pusher has front shoulders 150 and rear shoulders 152 which ride on the rails 146 of the latch. Below the front shoulders of the push rod extend dual stripper fingers 154 which fit through the slot 144 of the latch and push the clip body 7 of the ligation clip 3 in the feed position.

Figure 17:
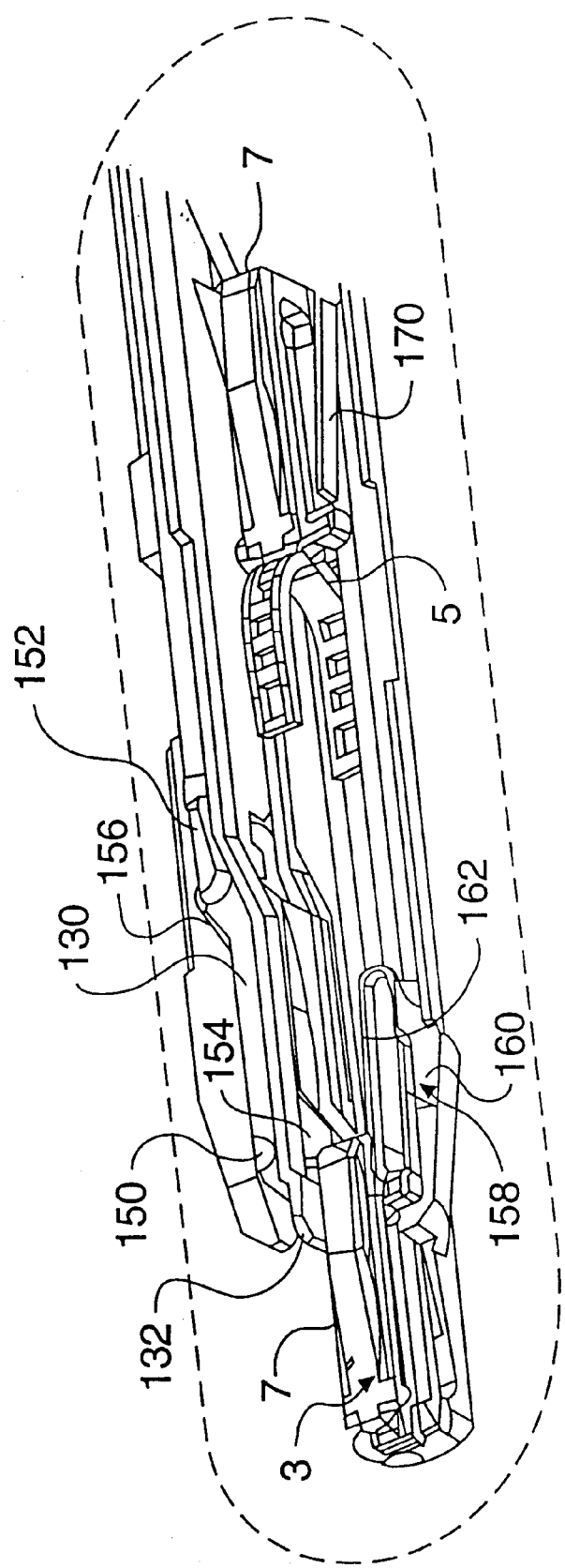
FIG. 17 is an enlarged perspective view of the distal end of the shaft portion shown in FIG. 16.

When the laparoscopic clip applicator is at rest the push rod is in a retracted position and the pusher rests in the proximal end of the slot 144. In this at-rest, or retracted position, the latch 132 is unbiased and rests above a horizontal plane defined by the ligation clips. Thus, the small notch 149 is out of engagement with the ligation clip. When the push rod moves forward the pusher advances toward the distal end of the shaft as it rides over the rails and is guided lower by a raceway ramp 156 formed in the magazine halves. This downward movement lowers the flexible latch to engage, with the notch 149, the lug of the designated ligation clip so as to hold the clamp 5 stationary. As the push rod continues in the distal direction, the stripper fingers 154 of the advancing pusher push the clip body 7 forward to close the clamp 5 of the ligation clip. The fully advanced position of the pusher is illustrated in FIG. 17 and shows the ligation clip in the fully closed position.

When the push rod is retracted, it pulls the pusher along the guide rails 146 of the latch toward the proximal end of the slot 144. Once the pusher passes under the raceway ramp 156, the biased latched will flex upwardly, returning to its unbiased position, and release its hold on the lug of the ligation clip. A kick spring 158 is positioned at the distal end of the shaft, as best seen in FIG. 17, to help release the closed ligation clip. With reference to FIGS. 15 through 17, the generally U-shaped kick spring includes a base portion 160 which fits in raceways in the shaft and a flexible portion 162 which is biased toward the base when positioned below the designated ligation clip. When the clip is destabilized, i.e., when the clip is fully closed and the latch releases the lug, the flexible portion of the kick spring exerts an upward force on the closed ligation clip to help force it out of the shaft. The kick spring is preferably stamped out of thin metal.

The advancer 134, the push rod 136 and the sprocket gear 140 combine together to form ligation clip feeding means. As briefly discussed above, the advancer and the push rod both include double-sided notched portions which engage with the sprocket gear. As shown in FIG. 15, notched portion 142 of the advancer is at its proximal end, and notched portion 138 of the push rod is at its central portion. Each notched portion has two opposite rows of notches, with the notches of one row being offset from the notches of the opposite row.

Figure 18:
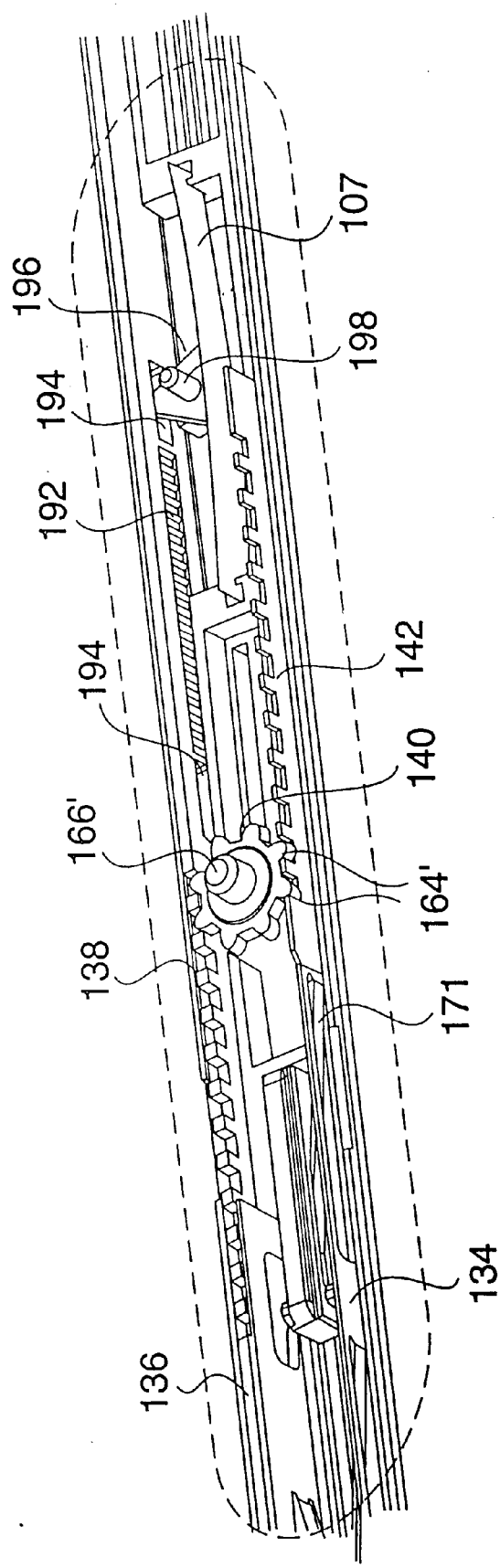
FIG. 18 is an enlarged perspective view of a central portion of the shaft portion shown in FIG. 16.

The sprocket gear 140 is preferably formed from two sprocket halves 141 and 143. Each sprocket half has a circumferentially spaced set of teeth 164 and 164', a pin 166 and 166' and an internal key 168 and 168' for mating together and securing the sprocket halves together. The pins are received in openings 170 and 170' in respective magazine halves 124 and 126 to rotatably support the sprocket gear. As best seen in FIG. 18, the sprocket gear is positioned between the notched portions of the push rod and the advancer. The teeth 164 and 164' are offset from each other, in other words, they are not aligned in the rotating axis direction of the pins, such that each set of teeth mates with one row of notches in each notched portions 138 and 142. As depicted in FIG. 18, the set of teeth 164' mate with a near side row of notches in notched portions 138 and 142. Unshown in FIG. 18 is the set of teeth 164 mating with the far side row of notches in notched portions 138 and 142. With the dual sprocket arrangement providing two sets of offset teeth and corresponding rows of offset notches, substantially twice the linear movement of the advancer can be achieved by rotation of the sprocket gear than if the respective teeth and notches were not offset or if only one set of comparably sized teeth and notches were used.

The clip feeding means works in the following manner. The advancer 134 is provided to advance the array of ligation clips by sliding back and forth through its engagement with the sprocket gear. A plurality of leaf springs 171 are preferably punched out of the thin metal advancer. Each leaf spring is connected to the advancer at its proximal end and engages one of the ligation clips when the advancer moves forward.

To advance the array of ligation clips, the advancer is slid in the rearward direction toward the handle assembly, where the leaf springs 171 are urged downwardly as they slide under the ligation clips. This movement is initiated by sliding the push rod in the forward direction, which causes the sprocket gear to rotate in the counterclockwise direction and retract the advancer. FIGS. 16 and 18 illustrate the advancer in the retracted position.

To start forward movement of the advancer, the push rod is retracted to rotate the sprocket gear in the clockwise direction. As best seen in FIG. 18, clockwise rotation of the sprocket gear will force the advancer in the forward direction. As the advancer is forwardly advanced, each leaf springs engages a lower side of one of the clip bodies 7 and drives the ligation clips forwardly. The forward movement of the advancer moves the ligation clips sequentially forward so the next-to-distal-most ligation clip advances into the feed, or designated, position.

A brake 172 and a hold 174 combine together to stabilize movement of the ligation clips in the shaft. Both the brake and the hold are stationary in raceways in the shaft and do not move. As best seen in FIG. 15, the brake and the hold are slender components preferably formed of thin metal. The hold acts like a ratchet mechanism to prevent rearward movement of the ligation clips but allow forward movement. This is accomplished by providing a plurality of flexible, downwardly bent leaf springs 176 each secured at its proximal end to a main body of the hold 174. Each leaf spring is positioned to engage one Y-shaped clamp 5 of the ligation clip from behind and prevent its movement in the rearward direction. When the ligation clips are advanced in the forward direction, the leaf springs are flexed upwardly and do not inhibit forward movement.

To complement the hold, the brake 172 is designed to limit excessive forward movement of the ligation clips. To accomplish this the brake has an array of punched stops 178 with downwardly extending nose portions 180. The nose portions will deter the ligation clips from sliding forward by abutting an upper portion of the clip. However, the stops 178 will flex upwardly, allowing the ligation clips to pass, when the clips are biased forwardly by the advancer.

The brake 172 and hold 174 are substantially the same width and length and both can be punched out of thin metal. The brake sits atop the hold and the nose portion 80 extends through an opening formed by the punched out leaf springs 176.

Figure 19:
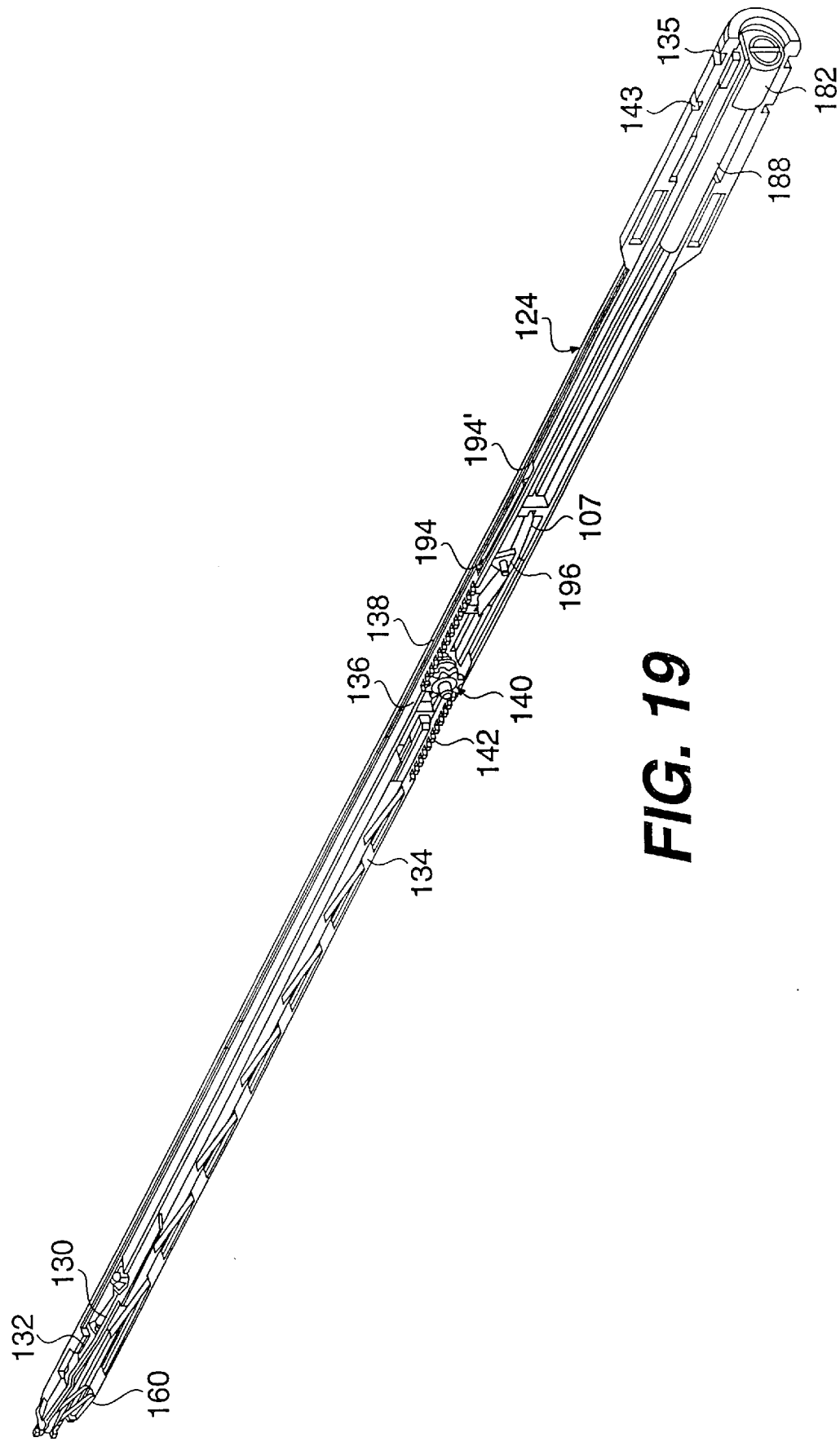
FIG. 19 is a perspective cross-sectional view of the shaft portion of the ligation clip applicator in accordance with the second embodiment of the present invention.

Axial movement of the push rod 136 to actuate the clip closing means and the clip feeding means is accomplished by a series of components shown in FIGS. 15, 16 and 19. A generally cylindrical spring block 182 is received in a large chamber 184 at the proximal end of the shaft for reciprocal movement. One face of the spring block is flat and provided with a key 185 to be received in a complimentary slot 186 at the proximal end of the push rod. Other means for connecting the spring block to the push rod can be used without departing from the scope of the invention. The spring block has an internally keyed surface for receiving a key 187, which is connected to the proximal end of an extended pin 188. A spring 189 is mounted on the extended pin and rests in a narrow chamber 190 in the shaft. A distal end of the spring rests against one end of the narrow chamber 190, and thus the spring biases the spring block 182 toward the handle portion. In its unbiased state, the spring block 182 is positioned at the proximal end of the large chamber 184, i.e., in the position shown in FIG. 19, and the push rod by virtue of its connection to the spring block 182, is positioned in its fully retracted position. As discussed in more detail below, the handle assembly is operated to slide the spring block back and forth within the large chamber and actuate the push rod.

The applicator is also provided with bi-directional locking means for ensuring that once a forward or rearward stroke is started, that stroke must be completed before a stroke in the other direction can begin. With reference to FIGS. 15 through 17, this is accomplished by providing on the push rod an engaging portion formed by ridges, or teeth, 192 flanked on one side by a distal slot 194 and on the other side a proximal slot 194'. A triangular pawl 196 is rotatably secured by a pawl pin 198 mounted in blocks 101 in the left and right magazines. A pawl leaf spring 107 is mounted in slots 105 in each magazine half. At the end of either stroke the pawl is positioned in one of the slots 194 or 194'.

When the push rod is in the fully actuated forward position as shown in FIGS. 16 and 18, an apex of the triangular pawl is oriented in its center position in proximal slot 194'. As the push rod is retracted, i.e., moved in the rearward direction, the distal side of the slot 194' will contact the pawl to rotate it slightly in the clockwise direction, just enough so the apex of the pawl, which will be referred to hereafter as an engaging apex, releases from the slot 194' and engages the ridges 192. This slight rotation of the pawl flexes the pawl spring 107 downwardly. As the push rod slides in the rearward direction, the ridges in the engaging portion ride over the engaging apex. At this point the push rod cannot reverse its sliding direction because the engaging apex, which remains rotated slightly off-center is positioned on a proximal side of the pawl pin 198 with respect to a vertical line extending orthogonally from the push rod to the pawl pin and defining a clearance distance. Because the distance from the engaging apex to the pawl pin is greater than the clearance distance, the pawl cannot rotate to the center position when it is engaged with the ridges. Only when the engaging pawl reaches one of the slots 194 or 194' can it rotate past the center position to allow the push rod to reverse its direction. The engaging apex can be truncated if necessary to allow for proper dimensioning within the shaft.

Figure 20:
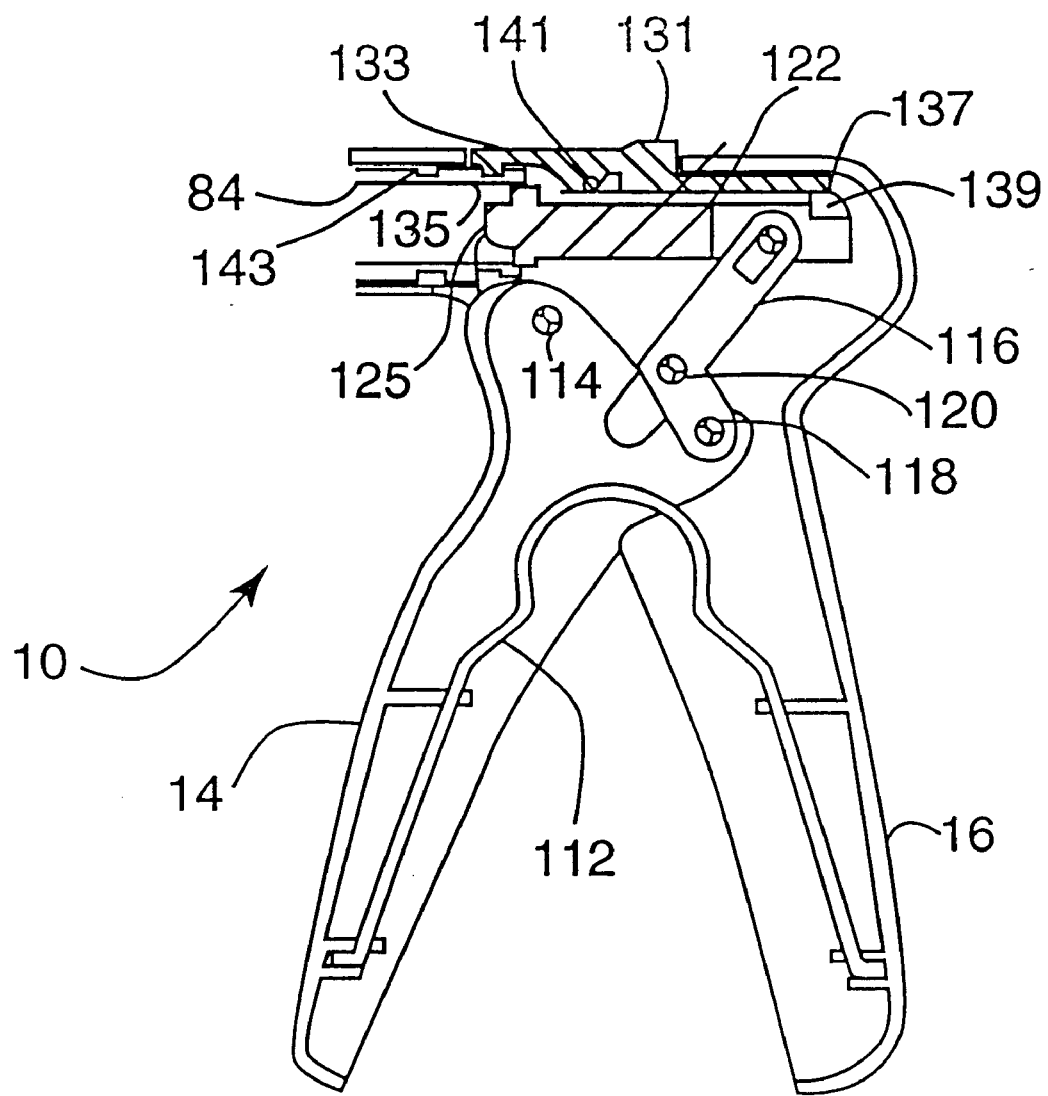
FIG. 20 is a vertical cross-sectional view of the handle assembly in accordance with the second embodiment.

FIG. 20 is a vertical cross-sectional view showing additional details of the handle assembly 10. The trigger 14 is biased to an opened position by a trigger spring 112 and pivots about a pivot point 114. A link 116 is connected to the trigger at pivot point 118 and pivots about pivot point 120 to axially slide an H-drive 122 within the large chamber 184 in the shaft. The H-drive is provided with an abutment end 125 for abutting the proximal end of the spring block 182 when the shaft portion is attached to the handle assembly.

As discussed above, the elongated shaft 12 and the handle assembly 10 are preferably separate elements that can easily be connected together. In this embodiment, a one-piece engagement latch 131 in the handle assembly 10 secures and locks the shaft 12 to the handle assembly. The distal end of the engagement latch is formed with a tooth 133 for engaging an annular groove 135 on the outer surface of the shaft. At the proximal end of the engagement latch a flexible member 137 engages a block 139 on the proximal end of the H-drive 122. As will be appreciated from the figure, a small space exists between the engagement latch 131 and the H-drive 122. This space allows the flexible member 137 to be depressed so as to pivot the engagement latch 131 about its pivot point 141 and raise the tooth 133 out of engagement with the annular groove 135. As a safety feature, when the H-drive slides in the forward direction, the block 139 moves toward the center of the engagement latch, thus preventing the flexible member from being depressed and locking the shaft to the handle assembly when the trigger is being squeezed. By providing an annular groove 135 on the shaft and an abutment end 125 on the H-drive 122, the shaft can be inserted into the handle assembly at any rotational orientation and will still be engaged and actuated by the handle assembly. A second annular groove 143 on the shaft receives an O-ring (unshown) for providing smooth rotational movement between the shaft and the handle assembly. Cylindrical grip 143 surrounds the proximal end of the shaft and allows the shaft to be rotated after engagement to the handle assembly.

FIG. 19 illustrates the manner in which the push rod 136 is actuated by operation of the handle assembly. In a push rod forward stroke initiated by squeezing the trigger 14, the H-drive 122 is forced forwardly to abut and slide the spring block 182 and thus the push rod in the forward direction toward the distal end of the shaft 12. As discussed above, the spring block is secured to push rod 136 by a key 185 engaged in slot 186 in the push rod. As the H-drive is driven in the forward direction by squeezing the trigger, the push rod and spring block slide forwardly in the distal direction. This forward motion causes the spring 188 to compress and become charged. Forward movement of the push rod actuates the clip assembly means as discussed above. When the trigger is fully squeezed, the pawl 196 travels past the ridged portion 192 and enters the distal slot 194.

The trigger is released in a push rod return stroke to retract the H-drive back to the at-rest position. Since the biasing force of the H-drive against the spring block is no longer in effect, the spring 188 discharges and pushes the spring block and push rod in the rearward direction.

The operational steps of the ligation clip applicator through one complete push rod forward stroke and push rod return stroke will be described below with reference to the figures. In the retracted position, the push rod 136 is fully retracted within the shaft by the force of spring 188. Thus, the latch 132 at the distal end of the shaft is positioned in its relaxed position to rest above the horizontal plane of the array of ligation clips 3, and the pusher 130 is positioned in the proximal portion of slot 144 in the latch. In addition, the advancer 134 is in its distal-most position, and the apex of pawl 196 is engaged in distal slot 194 in the push rod. As will be appreciated, in the retracted position, the sprocket 140 engages a distal end of the notched portion 138 in the push rod and a proximal end of the notched portion 142 of the advancer. FIG. 19 illustrates the components as positioned when the push rod is retracted.

When the trigger is actuated in the push rod forward stroke, the sliding H-block 122 abuts the spring block 182 and the push rod begins to slide forwardly. With this forward motion, the pawl 196 is biased to flex pawl spring 107 slightly downwardly and releases from slot 194 into engagement with the distal end of ridged portion 192. This forward motion also begins to rotate sprocket gear 140 in the counterclockwise direction as notched portions 138 in the push rod engage with the offset teeth 164 and 164' of the sprocket gear. The teeth of the rotating sprocket gear in turn engage the notched portion 142 of advancer 134 and begin to retract the advancer. As the advancer retracts, the leaf springs 171 are flexed downwardly as they pass under the array of ligation clips.

With continued forward motion of the push rod, the pusher 130 slides toward the distal end of the shaft and is lowered when it slides under downwardly sloped raceway ramp 156 in the shaft. Downward movement of the pusher lowers latch 132 to engage the Y-shaped clamp 5 that is the first portion of the ligation clip and hold it stationary. As the pusher continues to ride along rails 146 of the latch, the stripper fingers 154 engage from behind the second portion of the ligation clip, that is the clip body 7, and push it forward with respect to the stationary Y-shaped clamp 5 to close the designated ligation clip. During the forward stroke of the push rod, the ridged portion 192 of the push rod rides over the engaging apex of pawl 196. As discussed above, the pawl will not allow the push rod to reverse its stroke until it reaches the opposite end slot 194'.

At completion of the push rod forward stroke, the pusher is in its distal-most position and the stripper fingers 154 have successfully closed the ligation clip as shown in the enlarged view of FIG. 17. Additionally, with reference to FIG. 18, pawl 196 has entered the proximal slot 194' on the right side of ridged portion 192, and sprocket gear 140 is now engaged with the proximal end of notched portion 138 and the distal end of notched portion 142. The advancer is thus in its retracted position and leaf springs 171 are in position behind each ligation clip in the array and ready to move the clips forward upon forward movement of the advancer.

The push rod return stroke is initiated when trigger 14 is released, allowing compressed spring 188 to drive the spring block and connected push rod rearwardly toward the proximal end of the shaft. Upon movement of the push rod in the rearward direction, pawl 196 is again forced against pawl spring 107 to allow the engaging apex to exit the proximal slot 194' and engage the ridged portion 192. At the distal end of the shaft, the pusher slides in the rearward direction along slot 144 and allows the latch to lift as it passes under raceway ramp 156. When the latch lifts, the closed ligation clip is ejected from the distal end of the shaft by both the force of kick spring 160 and a pushing force supplied by the advancing ligation clip immediately behind the closed clip. Rearward movement of the push rod rotates the sprocket gear 140 in the clockwise direction, which in turn advances the advancer in the forward direction to advance the ligation clips and place the next-to-most distal ligation clip in the designated position. The rotation of the sprocket gear as the trigger is released allows for smooth forward movement of the advancer, and provides controlled advancement of the ligation clips. As the push rod is retracted, engagement of the apex of pawl 196 with the ridged portion 192 prevents the push rod from reversing its direction until the pawl reaches the distal slot 194.

As discussed above, the last clip loaded into the shaft is a dummy clip designed to help eject the preceding clip by pushing it from behind. The clip body of the dummy clip is longer than the clip bodies of the other clips so the pusher cannot position itself behind the clip body. The dummy clip can therefore not be closed, thus signalling the user that the applicator is out of ligation clips. The shaft portion can then be separated from the handle assembly and properly disposed of, and the handle assembly is ready to be used again with a new, sterile shaft portion.

Thus it will be appreciated that the present invention provides a unique mechanism for closing a two-piece ligation clip in minimally invasive surgical procedures. Moreover, this invention provides such a mechanism for automatically advancing each of a plurality of stored ligation clips to a feed or designated position so that all clips can be applied without removing the applicator device from the surgical site. Still further, since the present invention is specifically designed to apply two-piece bioabsorbable ligation clips in a convenient and reliable manner, all of the advantages attendant on use of such clips are also achieved.

Although specific embodiments of the present invention have been described above in detail, it will be understood that this description is merely for purposes of illustration. Various modifications of and equivalent structures corresponding to the disclosed aspects of the preferred embodiment in addition to those described above may be made by those skilled in the art without departing from the spirit of the present invention which is defined in the following claims, the scope of which is to be accorded the broadest interpretation so as to encompass such modifications and equivalent structures.

What is claimed is:

1. A ligation clip applicator for applying each of a plurality of sequentially fed two-piece ligation clips, comprising:

a handle assembly having an actuator;

an elongated shaft having a proximal end connected to said handle assembly, said shaft housing a plurality of two-piece ligation clips, with a distal-most ligation clip in said shaft disposed in a feed position; and actuating means, disposed within said shaft, for assembling and sequentially feeding the ligation clips, said actuating means including a clamp for engaging a first piece of the ligation clip disposed in the feed position, a slidable driver for driving a second piece of the ligation clip disposed in the feed position, and a slidable cam operably engaged with said clamp and said driver and operable by actuating said actuator, wherein upon actuation of said cam in a cam-forward stroke said clamp engages the first piece of the ligation clip and holds it stationary and said driver drives the second piece in a forward direction to compress the first piece and close the ligation clip, said actuating means further comprises holding means having retaining springs for preventing movement of the ligation clips in a rearward direction, and an advancer operably connected to said cam and slidable relative to the ligation clips for sequentially advancing the ligation clips in the forward direction and positioning a next-to-distal-most ligation clip in the feed position in said shaft.

2. A ligation clip applicator according to claim 1, wherein said advancer comprises a plurality of springs which are flexed by said ligation clips when said advancer slides in the rearward direction and which engage and advance the ligation clips when said advancer is moved in the forward direction.

3. A ligation clip applicator according to claim 1, further comprising a spring-loaded addrive connected to said advancer, said cam being operably engaged by said addrive and moving said addrive in the rearward direction during a cam-return stroke to charge said spring-loaded addrive, wherein said addrive disengages from said cam near the end of the cam-return stroke and discharges forwardly to drive said advancer in the forward direction to engage and advance the ligation clips.

4. A ligation clip applicator according to claim 3, wherein said addrive includes an extended shafts and a compression spring disposed around said shaft.

5. A ligation clip applicator according to claim 3, further comprising a cam spring connected to said cam and supported in said shaft, wherein said cam spring is charged during the cam-forward stroke and discharges to initiate the cam-return stroke and retract said cam and compress said compression spring to charge said spring-loaded addrive.

6. A ligation clip applicator for applying a two-piece ligation clip, comprising:

a handle assembly having an actuator;

an elongated shaft having a proximal end connected to said handle assembly and housing a plurality of two piece ligation clips, with a distal-most ligation clip in said shaft disposed in a feed position at a distal end of said shaft;

ligation clip assembling means, disposed within said shaft, for assembling and closing a designated two piece ligation clip disposed in the feed position;

ligation clip feeding means, disposed within said shaft, for advancing the ligation clips in a forward direction within said shaft and positioning a next-to-distal-most ligation clip in the feed position;

a slidable cam operably connected to said handle assembly for movement in a forward direction in a cam-forward stroke and in a rearward direction in a cam-return stroke, wherein in the cam-forward stroke said slidable cam operably engages said ligation clip assembly means to assemble and close the designated ligation clip, and in the cam-return stroke said cam actuates said ligation clip feeding means to advance the ligation clips; and a cam spring connected to said cam and supported in said shaft, wherein said cam spring is charged during the cam-forward stroke and discharges to initiate the cam-return stroke and retract said cam in the rearward direction.

7. An automatic laparoscopic ligation clip applicator for applying two-piece ligation clips, comprising:

a handle having a squeezable trigger;

an elongated shaft assembly having a proximal end connected to said handle and housing a plurality of two-piece ligation clips arranged in an array, with a distal-most ligation clip in said shaft assembly disposed in a feed position;

a clamp disposed in shaft assembly for engaging a first piece of a designated ligation clip disposed in the feed position and holding the first piece stationary;

a driver slidably disposed in said shaft assembly for driving a second piece of the designated ligation clip in the forward direction to compress the stationary first piece and close the designated ligation clip;

a holding means disposed in said shaft assembly and having engaging portions for preventing the array of ligation clips from moving in a rearward direction in said shaft;

an advancer slidably disposed in said shaft assembly for engaging the array of ligation clips and advancing them in a forward direction;

a slidable cam disposed in said shaft assembly and actuated by said handle to slide in a forward direction in a cam-forward stroke and in a rearward direction in a cam-return stroke, said cam operably connected to said driver and said advancer; and a cam spring connected to said cam and supported in said shaft, wherein said cam spring is charged during the cam-forward stroke and discharges to initiate the cam-return stroke and retract said cam in the rearward direction.

8. A ligation clip applicator according to claim 7, further comprising an addrive connected to said advancer and driving said advancer in the forward direction to advance the array of ligation clips.

9. A ligation clip applicator according to claim 8, wherein said addrive comprises an addrive head, an elongated shaft connected to said addrive head, and a compression spring mounted on said elongated shaft, said compression spring being compressed by movement of said addrive head in the rearward direction.

10. A ligation clip applicator according to claim 9, said addrive head having a flexible latch engagable with an addrive slot in said cam, wherein said flexible latch engages said addrive slot in the cam-return stroke and said addrive is advanced in the rearward direction to compress said addrive spring, said latch disengages from said addrive slot near the end of the cam-return stroke and said addrive spring discharges to advance said addrive and advancer in the forward direction whereupon said advancer engages the array of ligation clips and moves them in the forward direction.

11. A ligation clip applicator according to claim 7, wherein said handle includes a ratchet mechanism connected to said trigger for preventing release of said trigger until a full cam-forward stroke is completed.

12. A ligation clip applicator according to claim 7, wherein said proximal end of said shaft assembly includes a collar engagable within said handle.

13. A ligation clip applicator according to claim 12, wherein said handle includes a latch engagable with said collar to secure said shaft assembly, said latch being actuable only when said trigger is in an at-rest position.

14. A ligation clip applicator for applying two-piece ligation clips, comprising:

a handle having a squeezable trigger;

an elongated shaft assembly having a proximal end connected to said handle and housing a plurality of two-piece ligation clips arranged in an array, with a distal-most ligation clip in said shaft assembly disposed in a feed position;

a clamp disposed in said shaft assembly for engaging a first piece of a designated ligation clip disposed in the feed position and holding the first piece stationary;

a driver slidably disposed in said shaft assembly for driving a second piece of the designated ligation clip in the forward direction to compress the stationary first piece and close the designated ligation clip;

a holding means disposed in said shaft assembly and having engaging portions for preventing the array of ligation clips from moving in a rearward direction in said shaft;

an advancer slidably disposed in said shaft assembly for engaging the array of ligation clips and advancing them in a forward direction; and a slidable cam disposed in said shaft assembly and actuated by said handle to slide in a forward direction in a cam-forward stroke and in a rearward direction in a cam-return stroke, said cam operably connected to said driver and said advancer, wherein in the cam-forward stroke said cam actuates said clamp to engage the first piece of the designated ligation clip and actuates said driver to slide in the forward direction and engage the second piece of the designated ligation clip to assemble and close the designated ligation clip.

15. A ligation clip applicator according to claim 14, wherein said clamp and said driver each have distal ends that extend upwardly above a horizontal plane containing the array of ligation clips, and said cam actuates said clamp and said driver by advancing in the forward direction and riding down said distal ends to bias them in the horizontal plane.

16. A ligation clip applicator according to claim 15, wherein said cam actuates said clamp and said driver in the cam-return stroke by advancing in the rearward direction and allowing said distal ends of said clamp and said driver to flex upwardly out of the horizontal plane.

17. A ligation clip applicator for applying each of a plurality of sequentially fed two-piece ligation clips, comprising:

a handle assembly having an actuator;

an elongated shaft extending in a longitudinal direction and having a proximal end connected to said handle assembly, said shaft housing a plurality of two-piece ligation clips, with a distal-most ligation clip in said shaft disposed in a feed position; and actuating means, disposed within said shaft, for assembling and sequentially feeding the ligation clips, said actuating means including a latch for engaging a first piece of the ligation clip disposed in the feed position, a slidable pusher for driving a second piece of the ligation clip disposed in the feed position substantially along the longitudinal direction, and a slidable push rod operably engaged with said pusher and operable by actuating said actuator, wherein upon actuation of said push rod in a push rod forward stroke said latch engages the first piece of the ligation clips and holds it stationary and said pusher drives the second piece in a forward direction to compress the first piece and close the ligation clip.

18. A ligation clip applicator according to claim 17, said actuating means further comprising a hold having retaining springs for preventing movement of the ligation clips in a rearward direction, and an advancer operably connected to said push rod and slidable relative to the ligation clips for sequentially advancing the ligation clips in the forward direction and positioning a next-to-distal-most ligation clip in the feed position in said shaft.

19. A ligation clip applicator according to claim 18, wherein said advancer includes a plurality of springs which are flexed by the ligation clips when said advancer slides in the rearward direction and which engage and advance the ligation clips when said advancer is moved in the forward direction.

20. A ligation clip applicator according to claim 18, said actuating means further comprising a sprocket gear rotatably disposed in said shaft, said sprocket gear engaged between a notched portion in said being rotated by sliding movement of said push rod to actuate said advancer.

21. A ligation clip applicator according to claim 20, wherein said sprocket gear includes first and second sprocket halves, with each sprocket half having circumferentially spaced teeth which are offset from each other, and said notched portions in said push rod and advancer contain first and second rows of notches offset from each other for engaging said teeth of said first and second sprocket halves.

22. A ligation clip applicator according to claim 17, further comprising locking means for ensuring that once said push rod is actuated in either the push rod forward stroke or a push rod rearward stroke that stroke will be completed before said push rod can be actuated in an opposite direction.

23. A ligation clip applicator according to claim 22, wherein said locking means includes a triangular pawl and pawl spring mounted in said shaft, and a pawl engaging portion on said push rod having a ridged portion disposed between first and second slots.

24. A ligation clip applicator according to claim 17, said actuating means further comprising a spring block operably connected to said push rod and slidably supported in said shaft and a compression spring biasing said spring block in a rearward direction, wherein said spring is charged during the push rod forward stroke and discharges to initiate a push rod return stroke and retract said push rod in the rearward direction.

25. A ligation clip applicator according to claim 17, further comprising engaging means for releasably engaging said handle assembly and said elongated shaft, said engaging means being actuable only when said actuator is in an at-rest position.

26. A ligation clip applicator according to claim 17, wherein said elongated shaft is formed to be received in a cannula thereby to be used in minimally invasive surgical procedures.

27. A ligation clip applicator for applying a two-piece ligation clip, comprising:
    a handle assembly having an actuator;
    an elongated shaft extending in a longitudinal direction and having a proximal end connected to said handle assembly and housing a plurality of ligation clips, with a distal-most ligation clip in said shaft disposed in a feed position at a distal end of said shaft;
    ligation clip assembling means, disposed within said shaft, for assembling and closing a designated ligation clip disposed in the feed position;
    ligation clip feeding means, disposed within said shaft, for advancing the ligation clips in a forward direction within said shaft and positioning a next-to-distal-most ligation clip in the feed position; and
    a slidable push rod operably connected to said handle assembly for movement in a forward direction in a push rod forward stroke and in a rearward direction in a push rod return stroke, wherein in the push rod forward stroke said slidable push rod operably engages said ligation clip assembly means to assemble and close the designated ligation clip, and in the push rod return stroke said push rod actuates said ligation clip feeding means to advance the ligation clips, wherein
    said ligation clip assembling means includes a latch for holding stationary a first piece of the designated ligation clip and a slidable pusher for driving a second piece of the designated ligation clip in the forward direction to compress the first piece and close the designated ligation clip.

28. A ligation clip applicator according to claim 27, wherein said pusher is engaged to said push rod and driven by said slidable push rod to slide relative to said latch in the forward and rearward directions.

29. A ligation clip applicator according to claim 27, wherein said ligation clip feeding means comprises a hold having retaining springs for preventing movement of the ligation clips in the rearward direction, and a slidable advancer operably connected to said push rod and sliding relative to the ligation clips for sequentially advancing the ligation clips in the forward direction to position the next-to-distal-most ligation clip in the feed position.

30. A ligation clip applicator according to claim 29, wherein said advancer comprises a plurality of springs which are flexed by the ligation clips when said advancer slides in the rearward direction and which engage and advance the ligation clips when said advancer is moved in the forward direction.

31. A ligation clip applicator according to claim 29, further comprising a sprocket gear rotatably disposed in said shaft, said sprocket gear engaged between a notched portion in said push rod and a notched portion in said advancer, and being rotated by sliding movement of said push rod to actuate said advancer.

32. A ligation clip applicator according to claim 31, wherein said sprocket gear includes first and second sprocket halves, with each sprocket half having circumferentially spaced teeth which are offset from each other, and said notched portions in said push rod and advancer contain first and second rows of notches offset from each other for engaging said teeth of said first and second sprocket halves.

33. A ligation clip applicator according to claim 27, further comprising locking means for ensuring that once said push rod is actuated in either the forward stroke or the rearward stroke that stroke will be completed before said push rod can be actuated in an opposite direction.

34. A ligation clip applicator according to claim 33, wherein said locking means includes a triangular pawl and a pawl spring mounted in said shaft, and a pawl engaging portion on said push rod having a ridged portion disposed between first and second slots.

35. A ligation clip applicator according to claim 27, further comprising engaging means for releasably engaging said handle assembly and said elongated shaft, said engaging means being actuable only when said actuator is in an at-rest position.

36. A ligation clip applicator according to claim 27, further comprising a slot in said shaft for receiving the ligation clips to load the ligation clips.

37. An automatic laparoscopic ligation clip applicator for applying two-piece ligation clips, comprising:

a handle having a squeezable trigger;

an elongated shaft assembly having a proximal end connected to said handle and housing a plurality of two-piece ligation clips arranged in an array, with a distal-most ligation clip in said shaft assembly disposed in a feed position;

a latch disposed in said shaft assembly for engaging a first piece of a designated ligation clip disposed in the feed position and holding the first piece stationary;

a pusher slidably disposed in said shaft assembly for driving a second piece of the designated ligation clip in the forward direction to compress the stationary first piece and close the designated ligation clip;

a hold disposed in said shaft assembly and having engaging portions for preventing the array of ligation clips from moving in a rearward direction in said shaft;

an advancer slidably disposed in said shaft assembly for engaging the array of ligation clips and advancing them in a forward direction;

a rotatable sprocket gear mounted in said shaft and engagable with said advancer; and a slidable push rod disposed in said shaft assembly and actuated by said handle to slide in a forward direction in a push rod forward stroke and in a rearward direction in a push rod return stroke, said push rod connected at its distal end to said pusher and engagable with said sprocket gear to slide said advancer.

38. A ligation clip applicator according to claim 37, wherein in the push rod forward stroke said push rod actuates said latch to engage the first piece of the designated ligation clip and actuates said pusher to slide in the forward direction and engage the second piece of the designated ligation clip to assemble and close the designated ligation clip.

39. A ligation clip applicator according to claim 38, wherein said latch has a distal end that rests in sits unbiased position above a horizontal plane containing the array of ligation clips, and said push rod advances said pusher in the forward direction to lower the distal end of said latch into the horizontal plane.

40. A ligation clip applicator according to claim 39, wherein said push rod pulls said pusher in the push rod return stroke in the rearward direction to allow the distal end of said latch to flex upwardly out of the horizontal plane.

41. A ligation clip applicator according to claim 37, wherein said sprocket gear is engaged between a notched portion in said push rod and a notched portion in said advancer, and is rotated by sliding movement of said push rod to actuate said advancer.

42. A ligation clip applicator according to claim 41, wherein said sprocket gear includes first and second sprocket halves, with each sprocket half having circumferentially spaced teeth which are offset from each other, and said notched portions in said push rod and advancer contain first and second rows of notches offset from each other for engaging said teeth of said first and second sprocket halves.

43. A ligation clip applicator according to claim 37, further comprising a spring operably connected to said push rod and supported in said shaft, wherein said spring is charged during a push rod forward stroke and discharges in a push rod return stroke to bias said push rod in a rearward direction.

44. A ligation clip applicator according to claim 37, further comprising a spring block and an attached key slidably disposed in a proximal end of said shaft and a spring mounted on said key and abutting said spring block, with said spring block connected to said push rod and actuated by said handle, wherein said spring is charged during the push rod forward stroke and discharges in the push rod return stroke to bias said push rod in a rearward direction.

45. A ligation clip applicator according to claim 37, wherein said proximal end of said shaft assembly includes a collar engagable within said handle.

46. A ligation clip applicator according to claim 45, wherein said handle includes a latch engagable with said collar to secure said shaft assembly, said latch being actuable only when said trigger is in an at-rest position.

47. A ligation clip applicator according to claim 37, further comprising a brake for limiting forward sliding movement of the ligation clips.

48. A ligation clip applicator according to claim 37, further comprising locking means for ensuring that once said push rod is actuated in either the forward stroke or the rearward stroke that stroke will be completed before said push rod can be actuated in an opposite direction.

49. A ligation clip applicator according to claim 48, wherein said locking means includes a triangular pawl and a pawl spring mounted in said shaft, and a pawl engaging portion on said push rod having a ridged portion disposed between first and second slots.

50. A ligation clip applicator for applying each of a plurality of two-piece ligation clips, each ligation clip including a clamp and a clip body movable relative to the clamp to close it about a vessel, said clip applicator comprising:

means for storing a plurality of the ligation clips in an array with a distal-most ligation clip in an application position, with the array extending in a longitudinal direction of the clip applicator;

means, provided at a distal end of the applicator, for releasably holding the clamp of the distal-most ligation clip at the application position;

means for moving the clip body in substantially the longitudinal direction of the clip applicator and relative to the clamp, held at the application position, thereby to close the clamp, with said moving means moving relative to said holding means and said moving means and holding means housed in said storing means;

means for releasing said holding means to free the now closed distal-most ligation clip from the application position; and means for advancing another ligation clip from the array to the application position, with said advancing means housed with said releasing means in said storing means and operably engaged with said releasing means such that the closed ligation clip is released as the another ligation clip is being advanced.

* * * * *

UNITED STATES PATENT AND TRADEMARK OFFICE
CERTIFICATE OF CORRECTION

PATENT NO. : 5,904,693

DATED : May 18, 1999

INVENTOR(S) : PAUL C. DICESARE ET AL.

It is certified that error appears in the above-identified patent and that said Letters Patent is hereby corrected as shown below:

COLUMN 7
   Line 42, "such a" should read --such as--.

COLUMN 11
   Line 45, "house" should read --housed--.

COLUMN 18
   Line 42, "shafts" should read --shaft--;
   Line 54, "two" should read --two---;
   Line 59, "two" should read --two---.

COLUMN 21
   Line 7, "clips" should read --clip--;
   Line 27, "said being" should read --said push rod and a notched portion in said advancer, and being--.

COLUMN 23
   Line 45, "sits" should read --its--.

Signed and Sealed this

Eighth Day of February, 2000

Attest:

Attesting Officer

Q. TODD DICKINSON

Commissioner of Patents and Trademarks